US006589791B1

(12) United States Patent
LaBudde et al.

(10) Patent No.: US 6,589,791 B1
(45) Date of Patent: Jul. 8, 2003

(54) STATE-VARIABLE CONTROL SYSTEM

(75) Inventors: Edward V. LaBudde, Westlake Village, CA (US); Paul J. Queeney, Jr., Irvine, CA (US)

(73) Assignee: Cartesian Technologies, Inc., Irvine, CA (US)

( * ) Notice: Subject to any disclaimer, the term of this patent is extended or adjusted under 35 U.S.C. 154(b) by 0 days.

(21) Appl. No.: 09/575,395

(22) Filed: May 22, 2000

Related U.S. Application Data

(60) Provisional application No. 60/135,131, filed on May 20, 1999.

(51) Int. Cl.$^7$ .................................................. B01L 3/02
(52) U.S. Cl. ....................... 436/55; 73/863.01; 137/7; 222/52; 222/55; 422/100; 436/180
(58) Field of Search ................... 436/55, 180; 422/100; 73/863.01; 137/7; 222/52, 55

(56) References Cited

U.S. PATENT DOCUMENTS

| | | |
|---|---|---|
| 3,512,173 A | 5/1970 | Damouth |
| 3,946,398 A | 3/1976 | Kyser et al. |
| 4,121,466 A | 10/1978 | Reichler et al. |
| 4,199,013 A | 4/1980 | Reich et al. |
| 4,223,558 A | 9/1980 | Schmider et al. |
| 4,278,205 A | 7/1981 | Binoche |
| 4,323,537 A | 4/1982 | Mody |
| 4,369,664 A | 1/1983 | Bunce et al. |
| 4,478,094 A | 10/1984 | Salomaa et al. |
| 4,530,463 A | 7/1985 | Hiniker et al. |
| 4,555,957 A | 12/1985 | Frankel et al. |
| 4,681,742 A | 7/1987 | Johnson et al. |
| 4,795,336 A | * 1/1989 | Shannon et al. |
| 4,818,492 A | 4/1989 | Shimizu |
| 4,858,172 A | * 8/1989 | Stern |
| 4,877,745 A | 10/1989 | Hayes et al. |
| 4,922,852 A | 5/1990 | Price |
| 4,926,701 A | 5/1990 | Tompkins |
| 4,944,922 A | 7/1990 | Hayashi |
| 5,004,159 A | 4/1991 | Kistner |
| 5,056,462 A | 10/1991 | Perkins et al. |
| 5,158,748 A | 10/1992 | Obi et al. |
| 5,324,480 A | 6/1994 | Shumate et al. |

(List continued on next page.)

FOREIGN PATENT DOCUMENTS

| | | |
|---|---|---|
| WO | WO 99/42752 | 8/1999 |
| WO | WO 99/42804 | 8/1999 |
| WO | WO 00/01798 | 1/2000 |

OTHER PUBLICATIONS

"The Root Locus", *Introduction to Control System Analysis and Design*, F.J. Hale, Prentice–Hall, Inc., @ 1973, pp. 137–164.

"Drops on Demand", *Modeling Axisymmetric Flows: Dynamics of Films, Jets, and Drops*, S. Middleman, Academic Press, Inc., @ 1995, pp. 97–102.

*Primary Examiner*—Jan Ludlow
(74) *Attorney, Agent, or Firm*—Knobbe, Martens, Olson & Bear, LLP

(57) ABSTRACT

The invention relates to a state-variable feedback control system for monitoring and optimally controlling the operation of a microfluidic aspirate dispense-system. A steady state operating pressure is determined from the fluid, flow and/or operational characteristics of the system. Measurements from one or more pressure sensors are part of the control strategy to derive information for active feedback control and/or to achieve the desired operating pressure. Advantageously, the control system adds to the versatility of the aspirate-dispense system, for example, by permitting rapid dispensing of drops of different size. The control system also desirably facilitates efficient, repeatable and accurate performance and reduces wastage of valuable reagents or fluid.

80 Claims, 15 Drawing Sheets

U.S. PATENT DOCUMENTS

| | | |
|---|---|---|
| 5,338,688 A | 8/1994 | Deeg et al. |
| 5,429,807 A | 7/1995 | Matson et al. |
| 5,474,744 A | 12/1995 | Lerch |
| 5,509,966 A | 4/1996 | Sykes |
| 5,529,756 A | 6/1996 | Brennan |
| 5,593,839 A | 1/1997 | Hubbell et al. |
| 5,593,893 A | 1/1997 | Kobashi et al. |
| 5,601,980 A | 2/1997 | Gordon et al. |
| 5,601,982 A | 2/1997 | Sargent et al. |
| 5,639,665 A | 6/1997 | Arai et al. |
| 5,658,802 A | 8/1997 | Hayes et al. |
| 5,738,728 A | 4/1998 | Tisone |
| 5,741,554 A | 4/1998 | Tisone |
| 5,742,304 A | 4/1998 | Richtsmeier et al. |
| 5,743,960 A | 4/1998 | Tisone |
| 5,744,305 A | 4/1998 | Fodor et al. |
| 5,747,102 A | 5/1998 | Smith et al. |
| 5,750,881 A | 5/1998 | Dorenkott et al. |
| 5,763,278 A | 6/1998 | Sickinger et al. |
| 5,811,306 A | 9/1998 | Komatsu |
| 5,886,716 A | 3/1999 | Heinzl et al. |
| 5,916,524 A | 6/1999 | Tisone |
| 5,925,732 A | 7/1999 | Ecker et al. |
| 5,927,547 A | 7/1999 | Papen et al. |
| 6,063,339 A | 5/2000 | Tisone et al. |
| 6,203,759 B1 | 3/2001 | Pelc et al. |

* cited by examiner

STATE-VARIABLE CONTROL SYSTEM

RELATED APPLICATIONS

This application claims the benefit of U.S. Provisional Application No. 60/135,131, filed May 20, 1999, hereby incorporated by reference.

BACKGROUND OF THE INVENTION

1. Field of the Invention

The present invention relates generally to the aspiration and dispensing of microfluidic quantities of fluid and, in particular, to a feedback control system for controlling and monitoring the operation of aspirate-dispense systems to provide optimal, efficient and versatile operation and performance.

2. Description of the Related Art

There is an ongoing effort, both public and private, to spell out the entire human genetic code by determining the structure of all 100,000 or so human genes. Also, simultaneously, there is a venture to use this genetic information for a wide variety of genomic applications. These include, for example, the creation of microarrays of DNA material on substrates to create an array of spots on microscope slides or biochip devices. These arrays can be used to read a particular human's genetic blueprint. The arrays decode the genetic differences that make one person chubbier, happier or more likely to get heart disease than another. Such arrays could detect mutations, or changes in an individual's chemical or genetic make-up, that might reveal something about a disease or a treatment strategy.

One typical way of forming DNA microarrays utilizes an aspirate-dispense methodology. An aspirate-dispense system aspirates ("sucks") reagent(s) from a source of single strands of known DNA and dispenses ("spits") them on one or more targets to form one or more DNA arrays. Typically, an unknown sample of DNA is broken into pieces and tagged with a fluorescent molecule. These pieces are poured onto the array(s); each piece binds only to its matching known DNA "zipper" on the array(s). The handling of the unknown DNA sample may also utilize an aspirate and/or dispense system. The perfect matches shine the brightest when the fluorescent DNA binds to them. Usually, a laser is used to scan the array(s) for bright, perfect matches and a computer ascertains or assembles the DNA sequence of the unknown sample.

Microfluidic aspirate-dispense technology also has a wide variety of other research and non-research related applications in the biodiagnostics, pharmaceutical, agrochemical and material sciences industries. Aspirate-dispense systems are utilized in drug discovery, high throughput screening, live cell dispensing, combinatorial chemistry and test strip fabrication among others. These systems may be used for compound reformatting, wherein compounds are transferred from one plate source, typically a 96 microwell plate, into another higher density plate such as a 384 or 1536 microwell plate. Compound reformatting entails aspirating sample from the source plate and dispensing into the target plate. In these and other applications it is desirable, and sometimes crucial, that the aspirate-dispense system operate efficiently, accurately and with minimal wastage of valuable reagents.

Conventional aspirate-dispense technologies and methods are well known in the art, for example, as disclosed in U.S. Pat. No. 5,743,960, incorporated herein by reference. These typically use pick-and-place ("suck-and-spit") fluid handling systems, whereby a quantity of fluid is aspirated from a source and dispensed onto a target for testing or further processing. But to efficiently and accurately perform aspirate and dispense operations when dealing with microfluidic quantities, less than 1 microliter ($\mu$L), of fluid can be a very difficult task. The complexity of this task is further exacerbated when frequent transitions between aspirate and dispense functions are required. Many applications, such as DNA microarraying, can involve a large number of such transitions.

Conventional aspirate-dispense technology, when applied at these microfluidic levels, can suffer from unrepeatable, inconsistent and slow performance, and also result in wastage of valuable reagent. This is especially true at start-up and during transient or intermittent operations. Moreover, conventional aspirate-dispense systems can be limited in their adaptability, for example, in providing a sufficiently quick response to changes in the desired fluid output.

Therefore, there is a need for improved technology and methodology that provides for efficient, repeatable, accurate and versatile aspirate-dispense operations when handling and transferring fluids in microfluidic quantities, while reducing wastage of such fluids.

SUMMARY OF THE INVENTION

The present invention overcomes some or all of the above limitations by providing a state-variable feedback control system for monitoring and optimally controlling the operation of a microfluidic aspirate dispense-system. A steady state operating pressure is determined from the fluid, flow and/or operational characteristics of the system. Measurements from one or more pressure sensors are part of the control strategy to derive information for active feedback control and/or to achieve the desired operating pressure. Advantageously, the control system adds to the versatility of the aspirate-dispense system, for example, by permitting rapid dispensing of drops of different size. The control system also desirably facilitates efficient, repeatable and accurate performance and reduces wastage of valuable reagents or fluid.

In accordance with one embodiment, the invention provides a method of actively controlling a fluid delivery system. The fluid delivery system generally comprises a dispenser hydraulically arranged in series with a direct current fluid source. The method comprises the step of determining a steady state dispense pressure based on the fluid dynamical characteristic equations of the system. The direct current fluid source is operated to cause the steady state dispense pressure to exist within the system. The dispenser and the direct current fluid source are then actuated to dispense precise and/or predetermined quantities of a fluid onto a target.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following

DETAILED DESCRIPTION OF THE PREFERRED EMBODIMENTS

Figure 1:
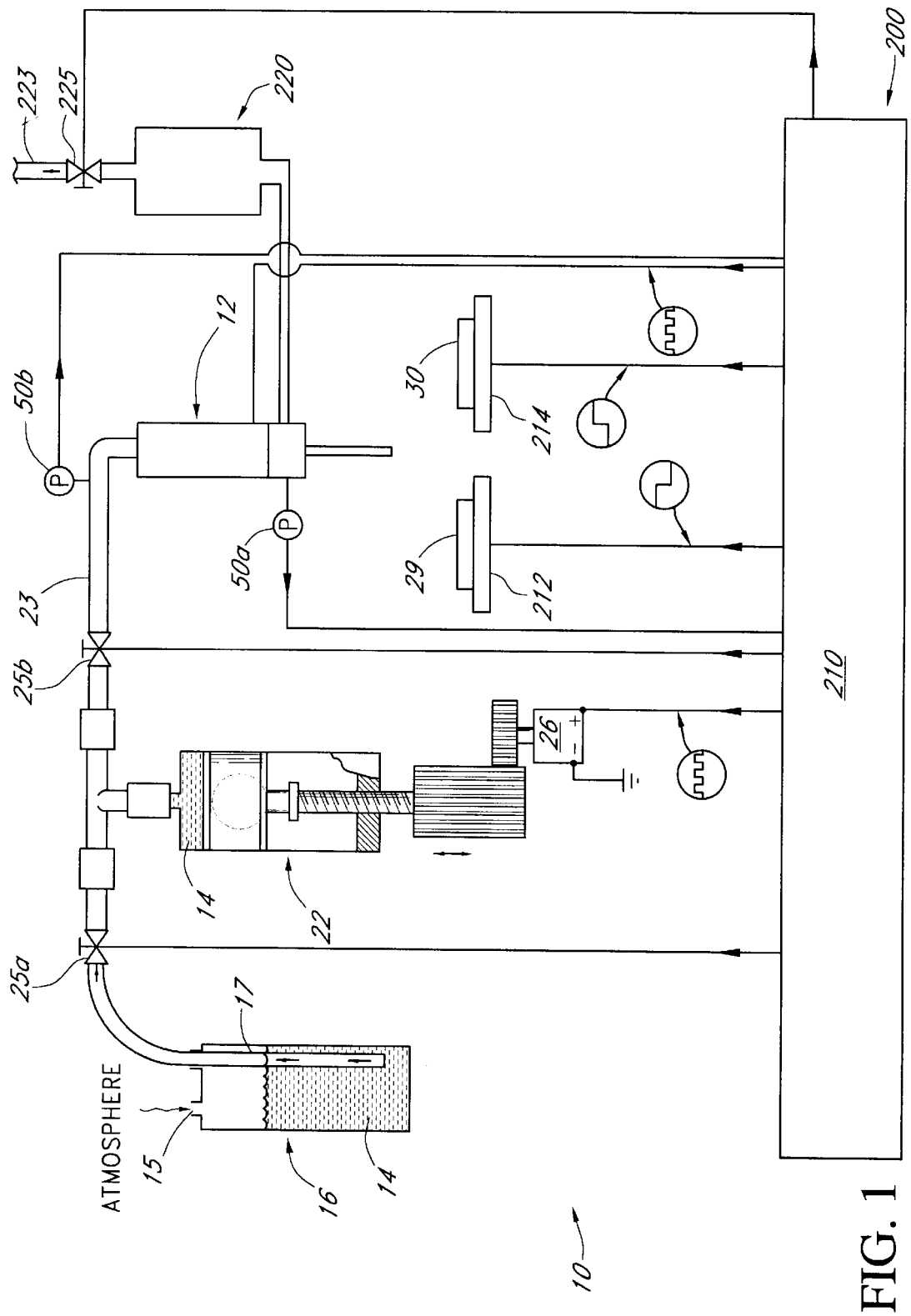
FIG. 1 is a simplified schematic illustration of a microfluidic aspirate-dispense system or apparatus having features in accordance with one preferred embodiment of the present invention.

FIG. 1 is a schematic drawing of a microfluidic aspirate-dispense apparatus or system 10 having features in accordance with one preferred embodiment of the present invention. The aspirate-dispense system 10 generally comprises a dispenser 12 hydraulically arranged in series with a positive displacement syringe pump 22 intermediate a reservoir 16. Preferably, and as discussed in greater detail later herein, the aspirate-dispense system 10 further comprises an automated feedback control system 200 to monitor and control the operation and performance of the aspirate-dispense system. 10. The control system includes a controller 210 and one or more pressure sensors 50 (labeled 50a, 50b) to monitor the pressure within the aspirate-dispense system 10 and provide diagnostic information about various fluid and flow parameters of the hydraulic system.

The dispenser 12 is used to aspirate a predetermined quantity of fluid or reagent from a source or receptacle 29 and dispense a predetermined quantity, in the form of droplets or a spray pattern, of the source fluid onto or into a target 30. The fluid source 29 can comprise a single-well receptacle, a multi-well microtiter plate or other suitable fluid source. The target 30 can comprise a glass slide, a substrate, a membrane, a multi-well microtiter plate or other suitable destination to which fluid or liquid is to be transferred.

The positive displacement pump 22 meters the volume and/or flow rate of the reagent aspirated and, more critically, of the reagent dispensed. The reservoir 16 contains a wash or system fluid, 14, such as distilled water, which fills most of the aspirate-dispense system 10. In some situations, where large quantities of the same reagent are to be dispensed, the reservoir 16 and syringe pump 22 can be filled with the reagent and the system 10 can be used purely for dispensing.

A robot arm may be used to maneuver the aspirate-dispense system 10 or alternatively the aspirate-dispense system 10 and/or its associated components may be mounted on movable X, X-Y or X-Y-Z platforms. In one preferred embodiment, the source 29 and target 30 are mounted or seated on respective movable X, X-Y or X-Y-Z platforms or tables 212, 214. The X, X-Y or X-Y-Z platforms or carriages 212, 214 provide relative motion between the platforms 212, 214 and the dispenser 12.

Also, multiple aspirate-dispense systems 10 may be utilized to form a line or array of dispensers 12. These multiple aspirate-dispense systems can include one or more state-variable control systems in accordance with the invention, as needed or desired, to control the system operation. Moreover, the state-variable control system of the invention can be used in conjunction with a multi-channel system comprising a manifold having a supply line or rail feeding into multiple independent channels with each manifold channel being in fluid communication with a respective dispenser.

The pump 22 is preferably a high-resolution, positive displacement syringe pump hydraulically coupled to the dispenser 12. Alternatively, pump 22 may be any one of several varieties of commercially available pumping devices for metering precise quantities of liquid. A syringe-type pump 22, as shown in FIG. 1, is preferred because of its convenience and commercial availability. A wide variety of other direct current fluid source means may be used, however, to achieve the benefits and advantages as disclosed herein. These may include, without limitation, rotary pumps, peristaltic pumps, squash-plate pumps, and the like, or an electronically regulated fluid current source.

Figure 2:
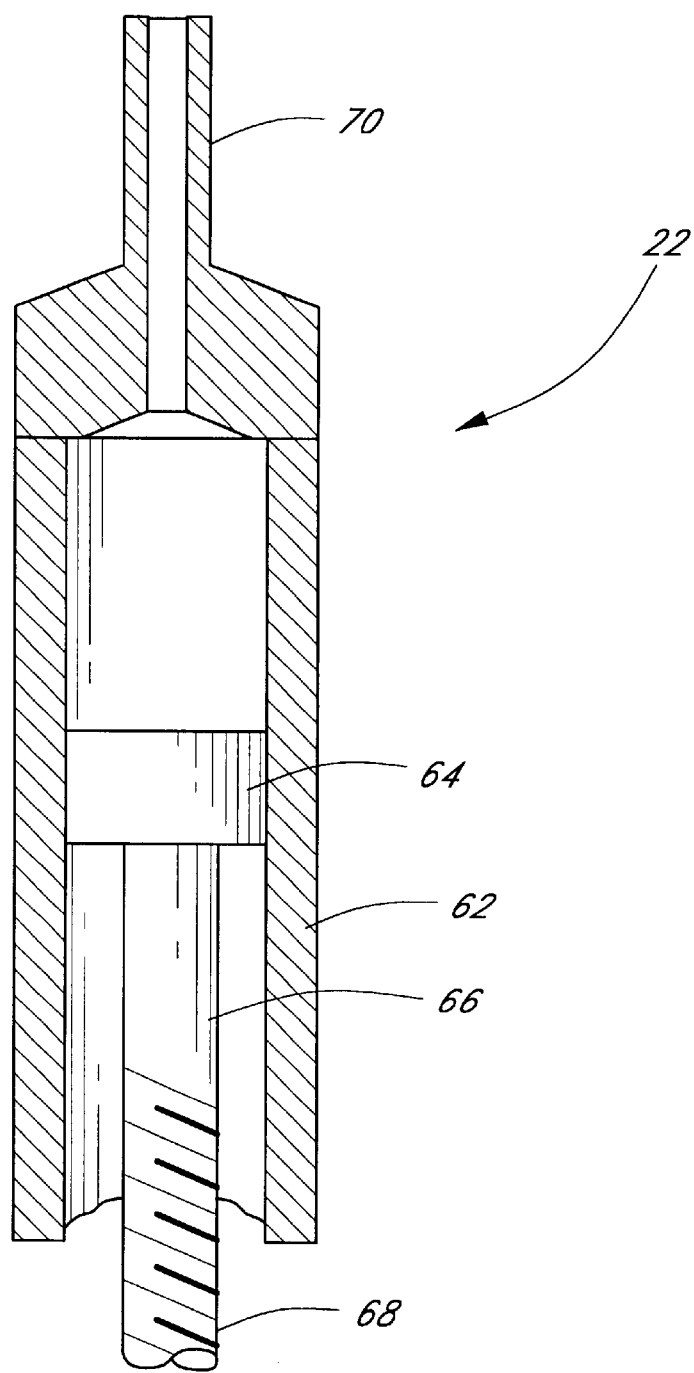
FIG. 2 is cross-sectional detail view of a syringe pump for use in the system of FIG. 1.

As illustrated in more detail in FIG. 2, the syringe pump 22 generally comprises a syringe housing 62 of a predetermined volume and a plunger 64 which is sealed against the syringe housing by O-rings or the like. The plunger 64 mechanically engages a plunger shaft 66 having a lead screw portion 68 adapted to thread in and out of a base support (not shown). Those skilled in the art will readily appreciate that as the lead screw portion 68 of the plunger shaft 66 is rotated the plunger 64 will be displaced axially, forcing system fluid from the syringe housing 62 into the exit tube 70. Any number of suitable motors or mechanical actuators may be used to drive the lead screw 68. Preferably, a stepper motor 26 (FIG. 1) or other incremental or continuous actuator device is used so that the amount and/or flow rate of fluid or reagent can be precisely regulated.

Referring to FIG. 1, the syringe pump 22 is connected to the reservoir 16 and the dispenser 12 using tubing 23 provided with luer-type fittings for connection to the syringe and dispenser. Various shut-off valves 25 (labeled 25a, 25b) and check valves (not shown) may also be used, as desired or needed, to direct the flow of fluid 14 to and/or from the reservoir 16, syringe pump 22 and dispenser 12. Typically, the valve 25b is in the open position. The valve 25a is in the closed position and is opened to draw fluid 14 from the reservoir 16 into the syringe pump 22, as and when needed.

The dispenser 12 (FIG. 1) may be any one of a number of dispensers well known in the art for dispensing a liquid, such as a solenoid valve dispenser, a piezoelectric dispenser, a fluid impulse dispenser, a heat actuated dispenser or the like. In one form of the present invention a solenoid dispenser 12, schematically illustrated in FIG. 3, is preferred.

Figure 3:
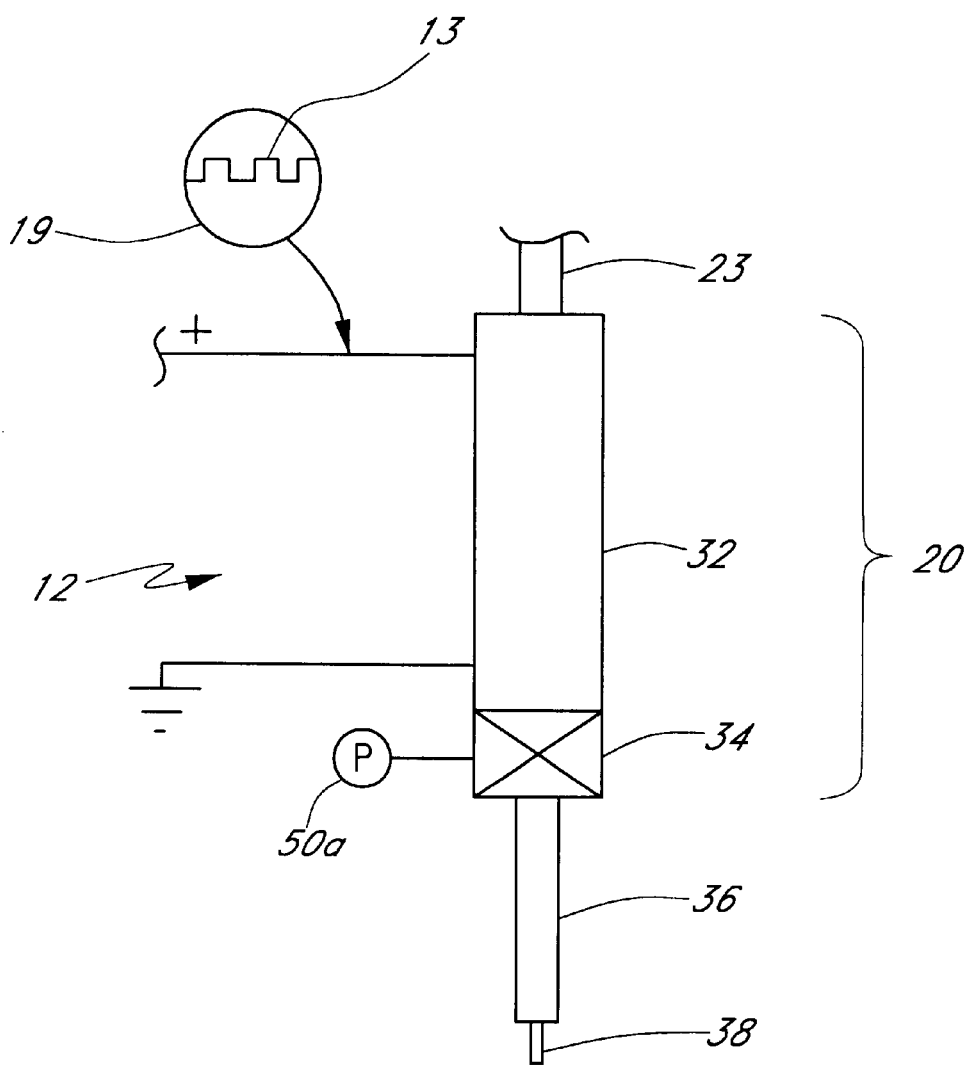
FIG. 3 is a schematic illustration of a solenoid valve dispenser for use in the system of FIG. 1.

Referring to FIG. 3, the solenoid valve dispenser 12 generally comprises a solenoid-actuated drop-on-demand valve 20, including a valve portion or cavity 34 and a solenoid actuator 32, hydraulically coupled to a tube, capillary or tip 36 and a nozzle 38. The solenoid valve 20 is energized by one or more electrical pulses 13 provided by a pulse generator 19. A detailed description of one typical solenoid valve dispenser can be found in U.S. Pat. No. 5,743,960, incorporated herein-by reference.

Referring again to FIG. 1, the wash fluid reservoir 16 may be any one of a number of suitable receptacles capable of allowing the wash fluid 14, such as distilled water, to be siphoned into pump 22. The reservoir may be pressurized, as desired, but is preferably vented to the atmosphere, as shown, via a vent opening 15. The particular size and shape of the reservoir 16 is relatively unimportant. A siphon tube 17 extends downward into the reservoir 16 to a desired depth sufficient to allow siphoning of wash fluid 14. Preferably, the siphon tube 17 extends as deep as possible into the reservoir 16 without causing blockage of the lower inlet portion of the tube 17. Optionally, the lower inlet portion of the tube 17 may be cut at an angle or have other features as necessary or desirable to provide consistent and reliable siphoning of wash fluid 14.

The aspirate-dispense system 10 is preferably configured to minimize the formation and accumulation of gaseous bubbles within the fluid residing in the system 10, and particularly in the dispenser 12 and feedline 23. For example, to minimize bubble formation, the components of the aspirate-dispense system 10 can be configured so that the fluid movements within the system avoid sharp local pressure drops, and hence gaseous bubble precipitation. Additionally, the components may be configured such that none or few "dead spots" are encountered by the fluid, thereby discouraging bubble accumulation within the system. These configurations can utilize suitably tapered inner cavities or lumens within the valve portion 34, tip 36 and/or nozzle 38 to provide relief from gaseous bubble precipitation and/or "dead spots."

In one preferred embodiment, the aspirate-dispense system 10 (FIG. 1) further comprises a suitably configured bubble trap 220. The bubble trap 220 is in fluid communication with the dispenser 12 and encourages the migration of gaseous bubbles to collect within the trap 220. By opening an open-close valve 225 in fluid communication with the bubble trap, the bubbles can be purged from the system by expelling them via an exit line or tubing 223. The exit tube 223 can lead to a waste position or to the reservoir 16.

The one or more pressure sensors 50 are provided at appropriate locations on the aspirate-dispense system 10. In one preferred embodiment, the pressure sensor 50a is situated at the valve portion or cavity 34. Alternatively, or in addition, the pressure sensor 50b can be placed intermediate the syringe pump 22 and the dispenser 12, such as on the feedline 23. In other preferred embodiments, one or more pressure sensors can be efficaciously placed at other suitable locations on the aspirate-dispense system 10, as required or desired, giving due consideration to the goals of providing suitably reliable system pressure data, and/or of achieving one or more of the advantages and benefits as taught or suggested herein.

Any one of a number of commercially available pressure sensors may be used in conjunction with the invention. The pressure sensors 50 are preferably differential pressure type devices. Preferably, the full scale pressure limit of the pressure sensors 50 is about 68,950 Pa (10 psig). Preferably, the pressure sensors 50 have a resolution of about 0.01% maximum, an accuracy of about 1% maximum and a bandwidth of about 5 kHz minimum. The elastic compliance at full scale pressure of the pressure sensors 50 should preferably allow a volume flow less than about $3 \times 10^{-10}$ m$^3$. In other preferred embodiments, the pressure sensors 50 can be configured and designed in alternate manners with efficacy, as required or desired, giving due consideration to the goals of providing suitably reliable system pressure data, and/or of achieving one or more of the advantages and benefits as taught or suggested herein.

The controller 210 is a system finite state machine (FSM) controller and generally comprises a host CPU or computer which interfaces with some form of data memory. The host CPU serves as the central controller and also the interface between the controller 210 and the user. It allows the operator to input dispensing and/or other data and to control, either independently or simultaneously, each aspect of the aspirate-dispense system 10 (FIG. 1).

The host CPU or computer of the system controller 210 has a slot or bus compatible to accept a plug-in circuit board. The circuit board or "controller card" preferably includes an AID converter having a resolution of about 14 bits or more, an accuracy of about 10 bits or more and a conversion speed of about 10 $\mu$sec (microseconds) or less. In other preferred embodiments, the resolution, accuracy and/or conversion speed can be selected otherwise with efficacy, as required or desired, giving due consideration to the goals of providing suitably accurate and fast data acquisition and control, and/or of achieving one or more of the advantages and benefits as taught or suggested herein.

The controller card of the system controller 210 preferably mounts or plugs into a computer bus providing data transfer and communication of instructions. The host CPU or computer also provides power to the controller card and further allows an operator to access, program and control the functions of the controller card. It is further contemplated that the host CPU or computer contains suitable computer software compatible with the host CPU (or computer) and the controller card which facilitates operation of the system as described herein.

Preferably, a display device and data input means are integral with the host CPU or computer thereby providing means to input data into a memory or static RAM array located on the controller card and to verify the same using the display device. As is known by those of ordinary skill in the art, a keyboard, mouse, trackball, light pen, capacitance touch screen, computer storage media are all acceptable data input means. Likewise, a color video monitor or screen provides a suitable display means.

Using a data entry device, such as a keyboard, an operator or user may enter data into the host CPU or computer in the form of a data array or graphical bit map to thereby instruct the electronic controller and aspirate-dispense system of the desired operation, parameters and characteristics. Conventional computer software may facilitate the entry of the data array or bit map via the host CPU to the memory of the controller card. The skilled artisan will recognize that a wide variety of computer systems, software and host CPUs may be efficaciously used with the present invention.

As illustrated in FIG. 1, the system controller 210 is interfaced with the dispenser 12, the pump stepper motor 26 and the motion platforms 212, 214 and provides electrical signals having frequency and duration to direct the operation of the aspirate-dispense system 10. The system controller 210 further receives pressure data from one or more of the pressure sensors 50. As discussed in detail later, this pressure data is processed and used to advantageously optimize the performance of the aspirate-dispense system 10. The system controller 210 can also be used to direct the opening and closing of any or all of the valves 25a, 25b and 225.

The skilled artisan will recognize that the hydraulic coupling between the pump 22 and the dispenser 12 of the aspirate-dispense system 10 provides for the situation where the input from the pump 22 exactly equals the output from the dispenser 12 under steady state conditions. Therefore, the positive displacement system uniquely determines the output volume of the system while the operational dynamics of the dispenser 12 serve to transform the output volume into ejected drop(s) having size, frequency and velocity.

It has been discovered, however, that within the aspirate-dispense system 10 there exists an elastic compliance partly due to the compliance in the delivery tubing and other connectors and components, and partly due to gaseous air bubbles that may have precipitated from air or other gases dissolved in the system and/or source fluid. As a result of this elastic compliance, initial efforts to dispense small quantities of fluid resulted in gradually overcoming the system compliance and not in dispensing fluid or reagent. Once this elastic compliance was overcome; a steady state pressure was found to exist and complete dispensing occurred thereafter. To understand this phenomenon and the features and advantages of the present invention, it is helpful to first discuss the theoretical predicted behavior and theoretical flow models relating to the positive displacement dispensing and aspirating system 10 of FIG. 1.

Theory of Operation for Positive Displacement Dispensing/Aspirating

The models included herein depict the basic fluid mechanical theory of operation of the positive displacement dispense/aspirate system of FIG. 1. Of course, the models may also apply to other direct current fluid source dispensing devices for dispensing small quantities of fluid. These models examine the design and operation of the dispensing system from a mathematical, physical, circuit and block diagram perspective representation, with each perspective being equivalent but offering a distinct view of the system.

Figure 4:
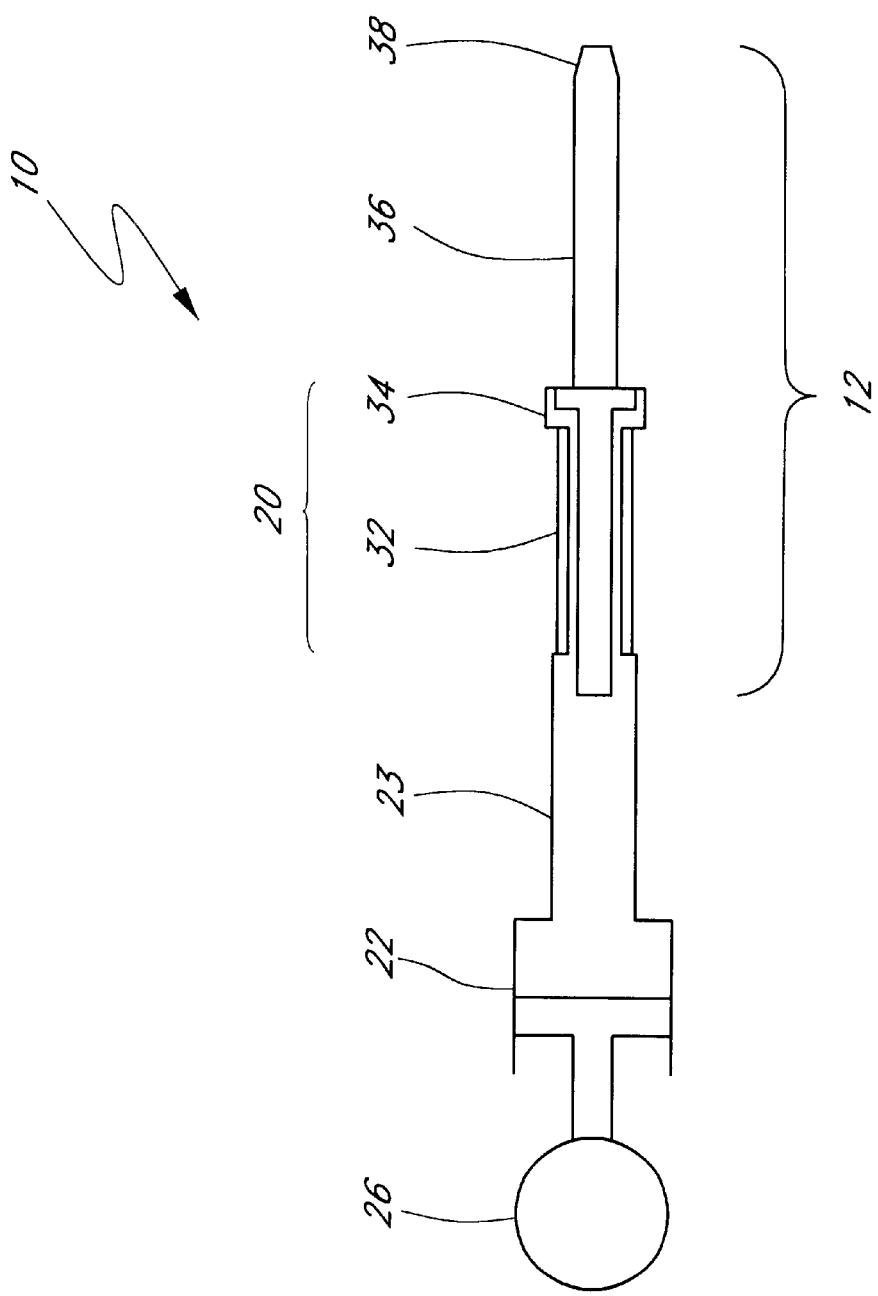
FIG. 4 is a simplified fluid circuit schematic of the positive displacement system of FIG. 1.

FIG. 4 is a simplified fluid circuit schematic drawing of the aspirate-dispense system or apparatus 10 of FIG. 1. The dispense system 10 generally comprises a dispenser 12 and a positive displacement syringe pump 22 driven by a stepper motor 26. The syringe pump 22 is hydraulically coupled to the dispenser 12 via a feedline 23. The dispenser 12 includes a drop-on-demand valve 20, such as a solenoid-actuated valve with a solenoid actuator 32 and a valve portion 34. The valve 20 is coupled to a tube or tip 36 and a drop-forming nozzle 38. The positive displacement pump 22 meters the volume and/or flow rate of the reagent or fluid dispensed. The dispenser 12 is selectively operated to provide individual droplets or a spray pattern of reagent, as desired, at the predetermined incremental quantity or metered flow rate. The dispenser 12 may also be operated in an aspirate mode to "suck" reagent or other liquids from a fluid source.

As noted above, the positive displacement pump 22 is placed in series with the dispenser 12 (FIGS. 1 and 4) and has the benefit of forcing the dispenser 12 to admit and eject a quantity and/or flow rate of reagent as determined (under steady state conditions) solely by the positive displacement pump 22. In essence, the syringe pump 22 acts as a forcing function for the entire system, ensuring that the desired flow rate is maintained regardless of the duty cycle, frequency or other operating parameters of the dispensing valve, such as the solenoid-actuated valve 20. This is certainly true for steady state operation, as discussed in more detail below. However, for non-steady state operation, it has been discovered that the elastic capacitance of the feedline and precipitated gaseous bubbles in the system can cause transient changes in dispensing pressure and system behavior.

A major part of the hydraulic compressibility or compliance within the system 10 (FIGS. 1 and 4) is due to precipitated air. The nominal solubility of air in liquids is in the range of about 2%. Even a small amount of this air converted to bubbles within the hydraulic system will dominate the compliance of the system 10. Thus, the dissolved air represents an important variable in determining the compliance or elastic capacitance, C, and hence determining the actuations of the drop-on-demand valve 20 and syringe pump 22 to bring the system to the desired predetermined and/or steady state pressure conditions (as discussed in greater detail herein below).

Preferably, the reagents or fluids used with the aspirate-dispense system 10 of the present invention are degassed, by using known surfactants. This reduces the influence of precipitated air in the system, and hence simplifies valve and pump actuations, and improved repeatability of the actuations to achieve the desired pressure conditions. Also, as indicated above, various components of the aspirate-dispense system 10 can be configured to reduce bubble precipitation and accumulation. Moreover, in one embodiment of the invention, the bubble trap 220 (FIG. 1) is provided. Nevertheless, despite whatever measures are taken, there will be at least some elastic compliance in the system which can cause transient variations in performance. These are discussed in more detail below.

In fluid flow analysis, it is typical to represent the fluid circuit in terms of an equivalent electrical circuit because the visualization of the solution to the various flow and pressure equations is more apparent. The electrical circuit components used in this analysis include flow resistance (R), elastic capacitance (C) and inertial inductance (L). As is known in the art, the electrical equivalent of hydraulic pressure, P, is voltage and the electrical equivalent of flow or flow rate, Q, is current. The following defines the basic mathematical characteristics of the components.

Resistance

Flow resistance, R, is modeled as a resistor in the equivalent circuit and can be mathematically represented by the following:

$$\frac{\partial P}{\partial Q} = R \tag{1}$$

In the case of fluid flow, the resistance is usually nonlinear because of orifice constrictions which give rise to quadratic flow equations. This is further elaborated below. In the present analysis it is assumed that laminar flow conditions are present and that fluid flows through a circular cross section. There are two types of flow resistance: capillary and orifice. Capillary flow resistance applies to flow through sections of tubes and pipes. Orifice flow resistance applies to constrictions or changes in flow direction. Capillary resistance can be represented by the following:

$$Q = A\bar{u} \tag{2}$$

$$R_c = \frac{\Omega L_c}{A_c} \tag{3}$$

$$\Omega = \frac{8\mu}{r_c^2} \tag{4}$$

where, $R_c$ is the capillary flow resistance, Q is the flow rate, $A_c$ is the cross-sectional area, $\bar{u}$ is the mean velocity of flow, $\Omega$ is the flow resistivity, $L_c$ is the capillary length, $\mu$ is the viscosity, and $r_c$ is the radius of the circular capillary.

Orifice resistance is represented as:

$$Q = \frac{\sqrt{\Delta P}}{R_o} \tag{5}$$

$$R_o = \frac{\sqrt{\rho/2}}{A_o C_d} \tag{6}$$

where, $R_0$ is the orifice flow resistance, $\rho$ is the fluid density, $A_0$ is the cross-sectional area, and $C_d$ is the discharge coefficient.

For a nozzle, the orifice constriction occurs at the entrance to the nozzle and the nozzle is modeled as a capillary (straight tube). This results in two resistances, orifice and capillary, in series. In general, the pressure and flow relationships in a system composed of a number of orifices and capillaries can be defined under these conditions as:

$$\Delta P = \Sigma R_o^2 Q^2 + \Sigma R_c Q \tag{7}$$

where $\Delta P$ is the pressure drop, the quadratic term $R_0^2 Q^2$ is due to the orifice resistance, which depends on the fluid density, and the linear term $R_c Q$ is due to the capillary resistance, which depends on the fluid viscosity. This suggests that for a given geometry it may be possible to measure these fluid properties (density and viscosity) by performing regression fits to pressure and flow data. In order to model the resistance, all the orifices and capillaries of the system need to be identified.

Inductance

In laminar fluid flow through capillaries, the fluid velocity profile is parabolic with zero velocity at the capillary wall and the maximum velocity at the center. The mean velocity $\bar{u}$ is one half the maximum velocity. Since the fluid has mass and inertia, there is a time constant associated with the buildup of flow in the tube. This is modeled as an inductance in series with the resistance. The derivation of the inertial time constant, $\tau$, is illustrated in *Modeling Axisymmetric Flows*, S. Middleman, Academic Press, 1995, Page 99, incorporated herein by reference. The time constant, $\tau$, can be defined as:

$$\tau = \frac{L}{R_c} = \frac{\rho r_c^2}{\mu a_1^2} \tag{8}$$

where L is the inductance and $a_1$=2.403. Thus, the inertial inductance can easily be computed from the time constant, $\tau$, and the capillary flow resistance, $R_c$.

Capacitance

The walls of the feedline, any precipitated gaseous bubbles in the fluid, and (to a very limited extent) the fluid itself are all elastic (compressible). This phenomenon gives rise to an elastic capacitance, where energy can be stored by virtue of the compression of the fluid and bubbles and/or the expansion of the feedline walls. The magnitude of the capacitance, C, can be found from the following equations:

$$Z_a = \rho C_s \tag{9}$$

$$Z_{ratio} = \frac{Z_a}{\Omega L} \tag{10}$$

$$C = \frac{L}{(Z_{ratio} R_c)^2} \tag{11}$$

where, $Z_a$ is the acoustic impedance and $C_s$ is the speed of sound. The speed of sound, $C_s$, accounts for the effects of fluid bulk modulus, wall elasticity, and elastic effects of any gas in the system. In the present modeling, the feedline is the major contributor to the elastic capacitance.

Physical Fluid Circuit Representation

The overall fluid circuit schematic construction of the positive displacement system 10 (FIG. 1) is shown in FIG. 4. As discussed before, the system 10 generally includes a stepper motor 26, a syringe pump 22, a feedline 23, and a drop-on-demand valve 20, with a solenoid actuator 32 and a valve portion or cavity 34 coupled to a tip 36 and a nozzle 38.

The syringe pump 22 (FIGS. 1 and 4) of the system acts as a fluid current source and forces a given volume per step into the system. The force available from the stepper motor 26 (FIGS. 1 and 4) is essentially infinite, due to the large gear ratio to the syringe input. The input is impeded from the forces feeding back from the system. Since volume, V, is the integral of the flow rate:

$$V = \int Q dt \tag{12}$$

and the flow rate, Q, is modeled as current, the syringe pump is therefore a current source rather than a pressure (voltage) source. Since any impedance in series with a current source has no effect on the flow rate, this has the beneficial effect of removing the influence of the impedance of the feed line (resistance and inductance) on the flow rate. Advantageously, this solves a major problem that would be present if a pressure source were used as the driving function. For a pressure source, the feedline impedance would offer a changing and/or unpredictable resistance to flow and could give rise to hydraulic hammer pressure pulses and varying pressure drops across the feedline which could affect the flow rate through the dispense system, and hence the fluid output. By utilizing a current source, such as the syringe pump, the effect of changes in fluid impedance is substantially negligible or none on the flow rate, and thus accurate and repeatable fluid volumes can be readily dispensed.

Electrical Circuit Analogue Representation

Figure 5:
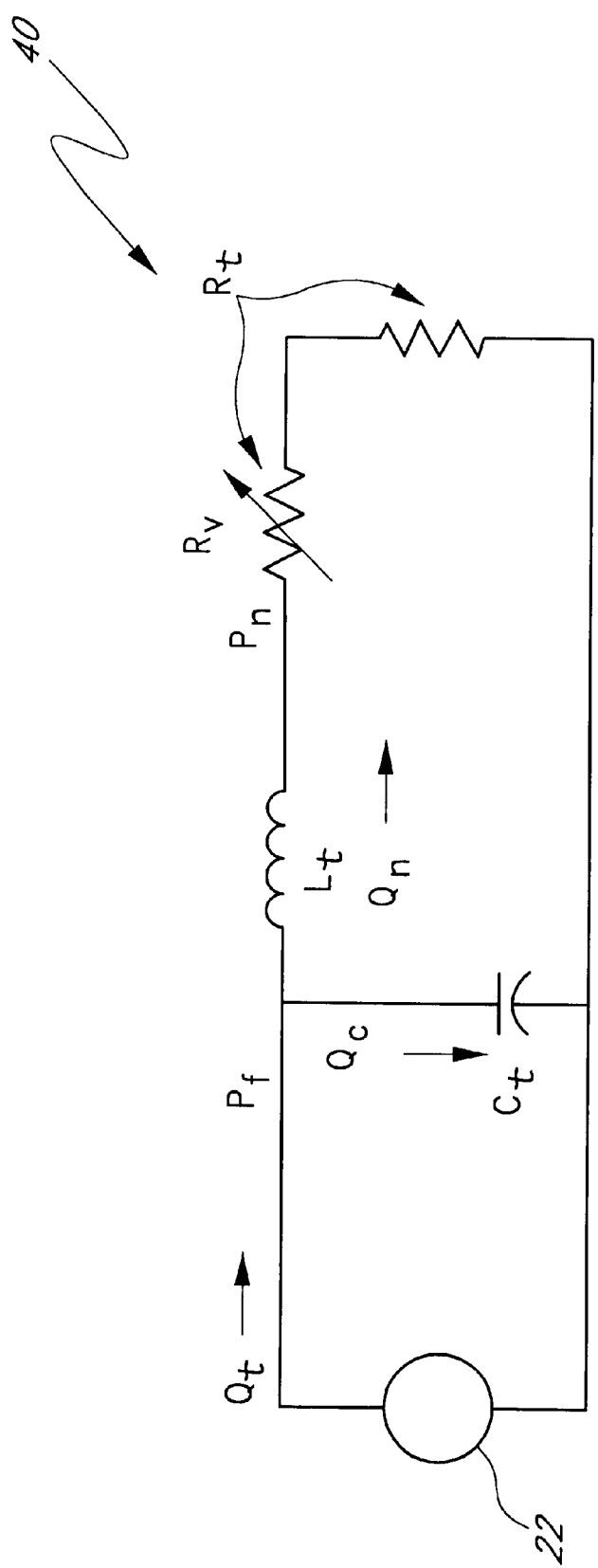
FIG. 5 is a simplified electrical circuit analogue representation of the fluid circuit schematic of FIG. 4.

A simplified electrical circuit analogue representation 40 of the positive displacement aspirate-dispense system fluid circuit schematic 10 (FIG. 4) is shown in FIG. 5. The syringe pump 22 forces a total flow rate of $Q_t$ into the system. The flow is comprised of $Q_c$ and $Q_n$. $Q_c$ is the flow that is driven into the elastic capacitance $C_t$ of the system and $Q_n$ is the flow rate that is output from the nozzle 38 of the system. The inductance $L_t$ and resistance $R_t$ are the totals of all elements within the valve 20, tip 36, nozzle 38 and feedline 23. The valve resistance $R_v$ varies with the actuation displacement of the valve 20 during operation from forces applied by the solenoid actuator 32. When the valve 20 is closed, the valve resistance $R_v$ is infinite. The pressure in the feedline 23 is $P_f$ and the pressure at the nozzle 38 is $P_n$.

Block Diagram Representation

Figure 6A:
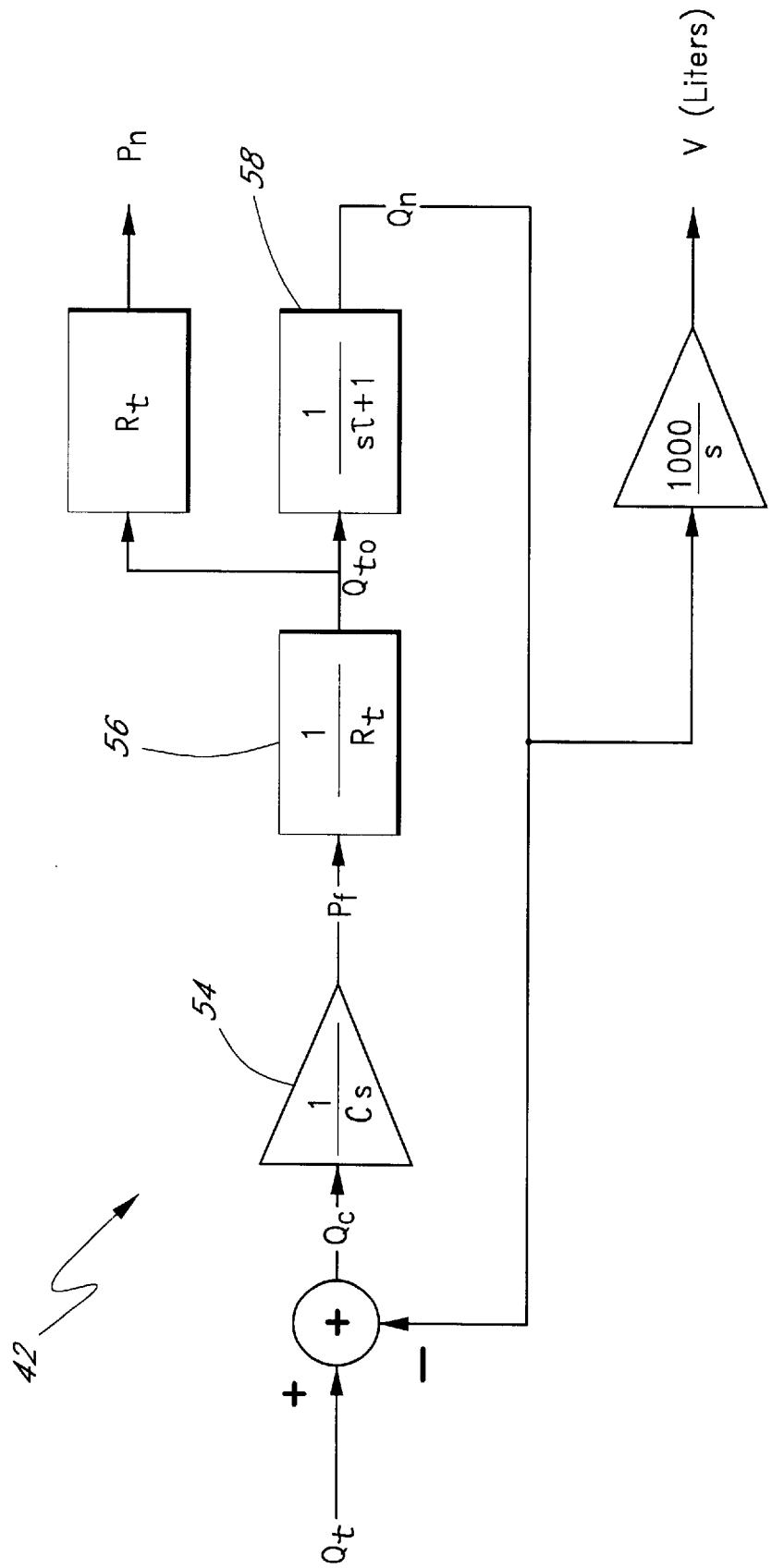
FIG. 6A is a control block diagram representation of the fluid circuit schematic of FIG. 4.

A block diagram or control system representation 42 of the positive displacement dispense aspirate-dispense system 10 fluid circuit schematic (FIG. 4) is shown in FIG. 6A. This is perhaps the best way to see why the output fluid volume is synchronized to the syringe input. As can be seen from FIG. 6A, this block diagram model 42 represents a feedback loop, in which the difference between $Q_1$ and $Q_n$ drives the flow into the elastic capacitance, $Q_c$. If the flow out of the nozzle 38 is not exactly the same as the flow input, $Q_t$, then the pressure in the feedline 23, $P_f$, will change. The feedback loop forces the value of $P_f$ to be whatever is necessary, at steady state, to maintain the output flow rate, $Q_n$, to equal the input flow rate, $Q_t$. This is true regardless of the value of $R_t$. The inductive time constant is $\tau$ (in FIG. 6A) and the Laplacian Operator is s=jω.

The value of feedline pressure, $P_f$, will increase when the valve 20 (FIGS. 3 and 4) is closed ($Q_n$=0), since all the input flow will go into the elastic capacitance as $Q_c$. The use of a time constant in the block diagram 42 (FIG. 6A) simplifies the mathematical calculations when the valve has infinite resistance. Qualitatively similar results will be obtained if the block diagram 42 (FIG. 6A) is modeled in a form including the unreduced Laplacian formula for inductance (L) instead of the simplified time constant (τ).

The block diagram model 42 (FIG. 6A) indicates that the system has the potential for damped oscillations in flow. The elastic capacitance is an integrator and the inertial time constant, τ, in the loop can give rise to the possibility of underdamped oscillations in transient flow. These oscillations may show up in pressure readings in the feedline 23 (FIGS. 1 and 4). The magnitude of the oscillations is dependent on the damping, which, in turn, is dependent on the flow resistance and the resonate frequency of the system.

The closed-loop transfer function of the control system 42 (FIG. 6A) may be generally stated as follows:

$$W(s) = \frac{G(s)}{1 + G(s)H(s)} \tag{13}$$

where:

W(s)=transfer function of the system expressed in the Laplace domain;
G(s)=forward transfer function; and
H(s)=feedback transfer function.

The forward transfer function G through blocks or control elements 54, 56, 58 (FIG. 6A) may be expressed as follows:

$$G(s) = \frac{1}{Cs}\frac{1}{R_t}\frac{1}{s\tau + 1} = \left(\frac{1}{R_t C \tau}\right)\frac{1}{s\left(s + \frac{1}{\tau}\right)} \tag{14}$$

Figure 6B:
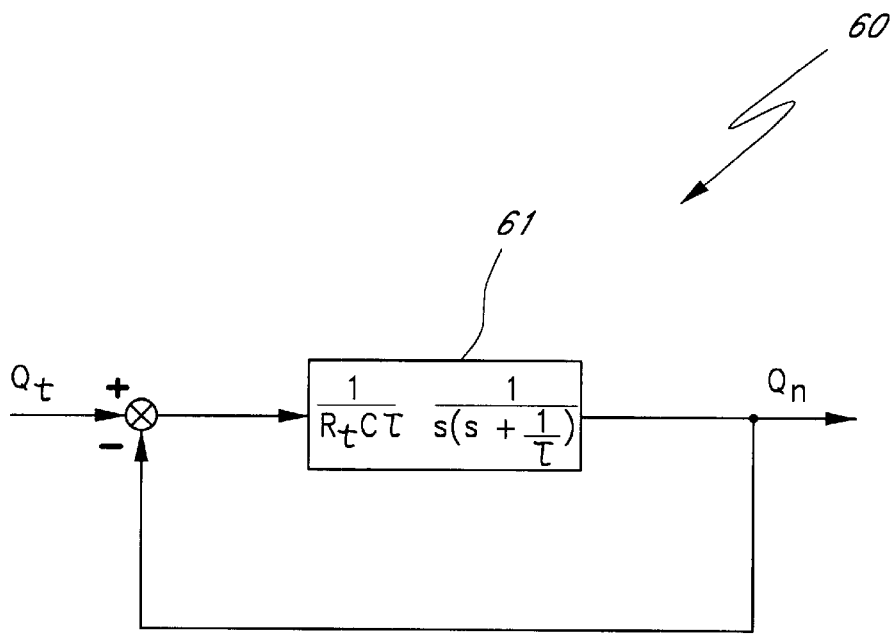
FIG. 6B is a simplified version of the control block diagram of FIG. 6A.

By using equation (14), the control block diagram 42 (FIG. 6A) can also be represented by a simplified equivalent block diagram 60 (FIG. 6B) with a block element 61 (FIG. 6B). The control or block element 61 (FIG. 6B) incorporates the reduced forward transfer function of equation (14). The feedback transfer function H for the block diagram 42 (FIG. 6A) may be expressed as follows:

$$H(s)=1 \tag{15}$$

Substituting equations (14) and (15) in equation (13), the unreduced closed-loop transfer function is expressed as:

$$W(s) = \frac{G(s)}{1 + G(s)H(s)} = \frac{Q_n}{Q_t} = \frac{\left(\frac{1}{R_t C \tau}\right)\frac{1}{s\left(s + \frac{1}{\tau}\right)}}{1 + \left(\frac{1}{R_t C \tau}\right)\frac{1}{s\left(s + \frac{1}{\tau}\right)}} \tag{16}$$

Equation (16) can be simplified to yield the closed-loop transfer function in a reduced form, as shown below by equation (17):

$$W(s) = \frac{Q_n}{Q_t} = \frac{1}{1 + (R_t C \tau)s\left(s + \frac{1}{\tau}\right)} \tag{17}$$

The characteristic equation of the control system 42 is defined by setting the denominator of equation (16) equal to zero and is given by:

$$1 + \left(\frac{1}{R_t C \tau}\right)\frac{1}{s\left(s + \frac{1}{\tau}\right)} = 0 \tag{18}$$

The zeros and poles of the characteristic equation can be determined by the expression:

$$K\frac{Z(s)}{P(s)} = G(s)H(s) = \left(\frac{1}{R_t C \tau}\right)\frac{1}{s\left(s + \frac{1}{\tau}\right)} \tag{19}$$

where, K is the gain and Z(s) and P(s) are polynomials which yield the zeros and poles. The above characteristic equation (18) has no zeros ($n_z$=0) and two poles ($n_p$=2) $P_1$=0 and $P_2=-1/\tau$, where $n_z$ is the number of zeros and $n_p$ is the number of poles. Also, the gain K of the system can be defined as:

$$K = \frac{1}{R_t C \tau} \quad (20)$$

The characteristic equation (18) can be manipulated to give a quadratic equation (21):

$$s^2 + \left(\frac{1}{\tau}\right)s + K = 0 \quad (21)$$

where K is the gain as defined above by the expression (20). Since equation (20) is a quadratic equation it has two roots which can be expressed as:

$$s_r = -\frac{1}{2\tau}\left[1 \pm \sqrt{1 - 4\tau^2 K}\right] \quad (22)$$

These roots $s_r$ determine the stability characteristics of the control system 42 (FIG. 6A). The nature of the roots. $s_r$ is dependent on the magnitude of the gain $K=1/(R_tC\tau)$, or more specifically on the magnitude of the parameter $(4\tau^2K=4\tau/R_tC)$. Note that since the time constant ($\tau$), the resistance ($R_t$), and the capacitance (C) are all positive real numbers, the parameter ($4\tau^2K$) is also a positive real number. The only exception to this is when the valve 20 (FIGS. 3 and 4) is closed, and hence the resistance $R_t$ is infinite which results in K=0, so that ($4\tau^2K$)=0.

For the case of $0<(4\tau^2K)\leq 1$, it is easily deduced that the characteristic equation (18) or (21) has two real roots $s_r<0$. This indicates that the control system 42 (FIG. 6A) is unconditionally stable for $0<(4\tau^2K)\leq 1$.

For the case of $(4\tau^2K)>1$, it is easily deduced that the characteristic equation (18) or (21) has two real complex conjugate roots $s_r$ which have negative real parts. This indicates that the control system 42 (FIG. 6A) is unconditionally stable for $(4\tau^2K)>1$.

For the case of $(4\tau/R_tC)=0$, that is when the valve 20 (FIGS. 3 and 4) is closed and the resistance $R_t$ is infinity (K=0), it is easily deduced that the characteristic equation (18) or (21) has two real roots $s_r=0$ and $s_r<0$. This indicates that the control system 42 (FIG. 6A) is limitedly stable for $(4\tau^2K)=0$ or K=0.

The above stability analysis shows that the control block representation 42 (FIG. 6A) of the fluid circuit schematic 10 (FIG. 4) of the positive displacement aspirate-dispense system 10 (FIG. 1) is always stable. This is true as the parameter $(4\tau^2K)$, or alternatively the gain K, is varied from zero to infinity.

Another popular technique for studying the stability characteristics of a control system involves sketching a root locus diagram of the roots of the characteristic equation as any single parameter, such as the gain K, is varied from zero to infinity. A discussion of the root locus method can be found in most control theory texts, for example, *Introduction to Control System Analysis and Design*, Hale, F. J., Prentice-Hall, Inc., 1973, Pages 137–164, incorporated herein by reference.

Figure 6C:
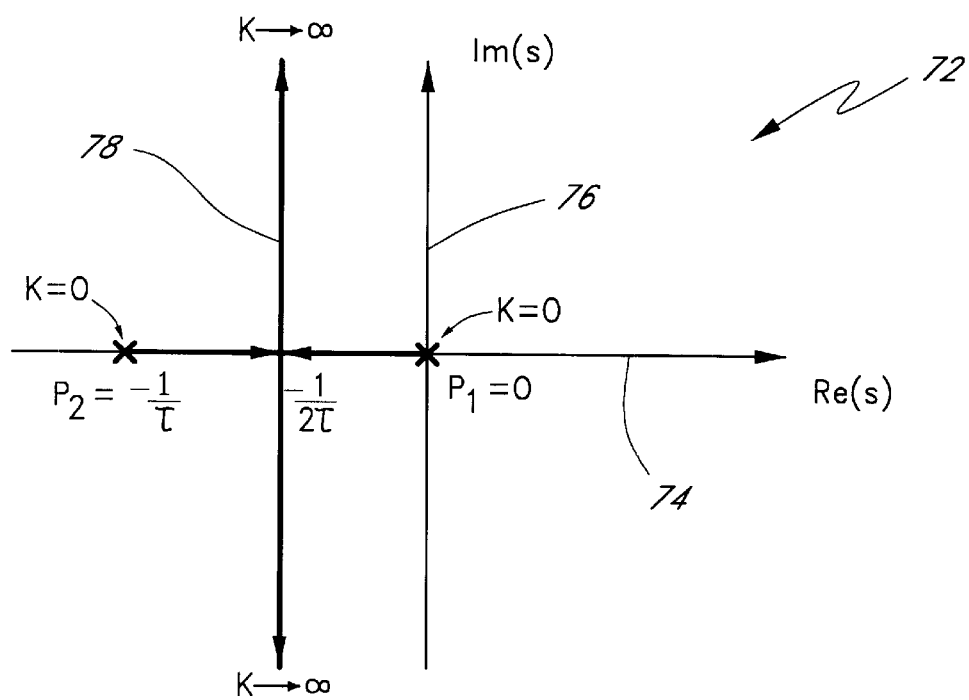
FIG. 6C is a root-locus diagram of the fluid circuit schematic of FIG. 4.

FIG. 6C shows a sketch of a root locus diagram 72 for the control system representation 42 (FIG. 6A). The root locus diagram 72 is plotted in the s-plane and includes a real axis 74, Re(s), an imaginary axis 76, Im(s), and a sketch of the root locus 78.

Typically, the determination of the root locus relies on a knowledge of the zeros and poles of the control system. As indicated above, the characteristic equation (18) of the control block diagram 42 (FIG. 6A) has no zeros ($n_z=0$) and two poles ($n_p=2$). Thus, the root locus 78 (FIG. 6C) will have two branches and two zeros at infinity. On the real axis 74 (FIG. 6C), the root locus will exist only between the two poles $P_1=0$ and $P_2=-1/\tau$. Since there are two infinite zeros, there will be two asymptotes to the locus branches at angles given by:

$$\theta_k = \frac{(2k+1)180°}{n_p - n_z} \quad k = 0, 1 \quad (23)$$

so that, $\theta_k=90°, 270°$. The cg or intersection of the asymptotes and the real axis 74 (FIG. 6C) is given by:

$$cg = \frac{\sum poles - \sum zeros}{n_p - n_z} \quad (24)$$

so that, $cg=-1/2\tau$. Since there are only two poles $P_1$ and $P_2$ on the real axis the breakaway point between the two poles, $P_1=0$ and $P_2=-1/\tau$, is halfway between the poles, that is, at $s=-1/2\tau$. Also, since two branches are leaving the breakaway point, the angles at breakaway are $\pm 90°$. This completes the sketch of the root locus 78 as shown in FIG. 6C.

The root locus 78 (FIG. 6C) begins at the poles $P_1=0$ and $P_2=-1/\tau$ with the gain K being equal to zero. The root locus 78 (FIG. 6C) then travels along the negative segment of the real axis 74 (FIG. 6C) while the value of K is incremented and converges at the breakaway point at $s=-1/2\tau$. At the breakaway point the root locus 78 (FIG. 6C) branches, parallel to the imaginary axis 76 (FIG. 6C), towards the zeros at infinity with the gain K being further incremented until it reaches infinity.

It will be appreciated that the root locus 78 (FIG. 6C) represents all values of s in the Laplace domain for which the characteristic equation (18) is satisfied as the gain K is varied from zero to infinity. From the root locus diagram 72 (FIG. 6C) it may be observed that all of the roots (except the root at the pole $P_1=0$) lie on the left side of the imaginary axis 76 in the s-plane. This indicates that the system is unconditionally stable for all possible values of the gain K>0 and the system is limitedly stable when the gain K=0. Thus, the control system representation 42 (FIG. 6A) of the fluid circuit schematic 10 (FIG. 4), and hence of the positive displacement aspirate-dispense system 10 (FIG. 1), demonstrates stability for all values of K. This concurs with the above stability analysis based on the solution for the roots of the characteristic equation (18) or (20).

It was demonstrated above that providing a positive displacement pump 22 in series with a dispenser 12 (FIG. 1) has the benefit of forcing the dispenser 12 to admit and eject a quantity and/or flow rate of reagent as determined solely by the positive displacement pump 22 for steady state operation. In essence, the syringe pump 22 acts as a forcing function for the entire system, ensuring that the desired flow rate is maintained regardless of the duty cycle, frequency or other operating parameters of the dispensing valve, such as the solenoid-actuated valve 20 (FIG. 3). With such configuration and at steady state operation one does not really care what the pressure in the system is because it adjusts automatically to provide the desired flow rate by virtue of having a positive displacement or direct current fluid source as a forcing function for the entire system.

However, this does not address the situation of latent and/or transient pressure variations, such as associated with initial start-up of each dispense and aspirate function. In particular, it has been discovered that the pressure in the system is of critical concern for non-steady state operation involving aspirating or dispensing of microfluidic quantities, typically less than about 50 microliters ($\mu$L), of liquid reagents or other fluids. Specifically, for an aspirate function it has been discovered that a system pressure close to or below zero is most preferred, while for a dispense function it has been discovered that a finite and positive predetermined steady state pressure is most preferred.

The transitions between various modes (aspirate, dispense, purge/wash) and/or flow rates or other operating parameters can result in pressure transients and/or undesirable latent pressure conditions within the positive displacement dispense/aspirate system. Purge and wash functions usually entail active dispensing in a non-target position. In some cases, when the same reagent is to be aspirated again, several aspirate-dispense cycles can be performed before executing a purge or wash function. Also, sometimes a purge function may have to be performed during a dispense function, for example, to alleviate clogging due to the precipitation of gaseous bubbles within the system and/or source fluid. Moreover, the accumulation of these bubbles can change the system compliance over time, and hence the desired optimum dispensing pressure.

Figure 7:
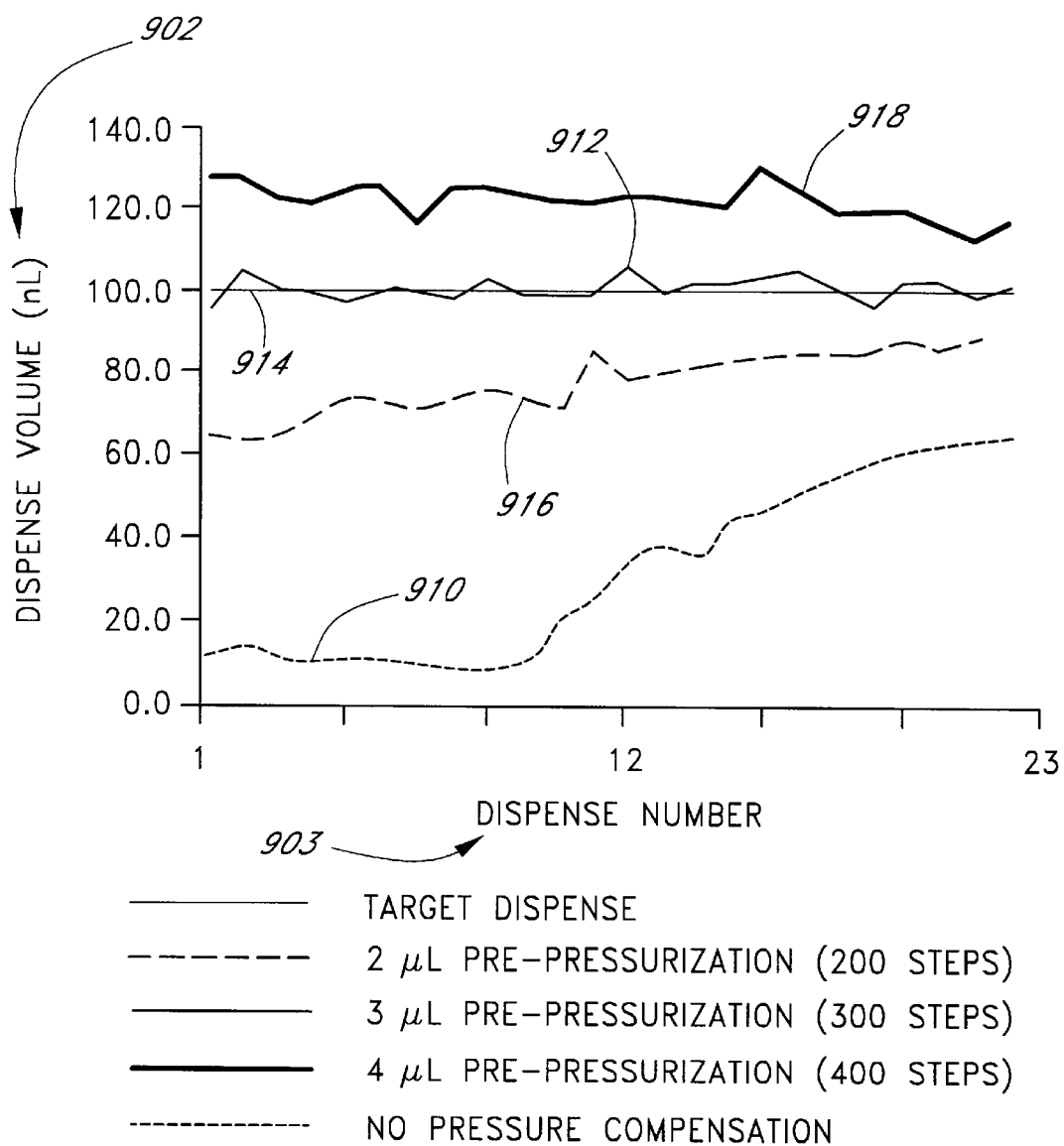
FIG. 7 is a graph illustrating non-steady state dispense volumes versus steady state dispense volumes and showing the beneficial effects of pressure compensation prior to dispensing.

For example, line 910 in FIG. 7 illustrates transient dispense effects caused by initial start-up of a dispensing system 10 (FIG. 1) in which no pressure compensation scheme is utilized. The x-axis 903 represents the dispense number or number of dispenses and the y-axis 902 represents the dispense volume, in nanoliters (nL) of each droplet or droplets dispensed. Line 914 in FIG. 7 represents the target dispense volume of 100 nL.

As can be seen by the data of FIG. 7, the non-pressure compensated (non-steady state) dispensed volume represented by line 910 is substantially smaller than the target dispense volume of 100 nL (line 914) since the system pressure at start-up is substantially lower than the desired steady state and/or predetermined pressure. The non-pressure compensated dispense volume (line 910) can be lower by a factor of about ten compared to the target dispense volume (line 914). Moreover, even after 23 dispenses (see FIG. 7) the dispensed volume (line 910) is still below the target volume (line 914).

Line 912 represents a series of about 100 nL dispenses performed in accordance with one preferred method of the present invention, wherein an optimized pressurizing (300 steps of the syringe plunger 64—shown in FIG. 2) is performed prior to dispensing. The pressure compensation scheme provides dispense volumes (line 912) which are in substantially close conformity with the target dispense volume (line 914) of 100 nL. Under-pressurization (200 steps of the syringe plunger 64), as illustrated by line 916, can result in dispense volumes that are undesirably less than the target dispense volume 914. Similarly, as illustrated by line 918, over-pressurization (400 steps of the syringe plunger 64) can result in dispense volumes that are undesirably more than the target dispense volume 914.

Automated Feedback Control System

The above discussion highlights the desirability of controlling the hydraulic pressure within a microfluidic aspirate-dispense system. The state-variable control system 200 (FIG. 1) of the present invention causes a steady state pressure to exist within a fluid delivery, transfer or handling system, such as the positive-displacement aspirate-dispense system 10 (FIG. 1), prior to initiating dispensing operations. The initial positive pressure overcomes the system's elastic compliance and thereby achieves a steady state pressure condition prior to dispensing. Advantageously, this assures that the fluid displaced by the syringe pump 22 (FIG. 1) will be completely transferred as output to the system nozzle, such as the nozzle 38 (FIG. 3).

The manner in which the active feedback control system 200 (FIG. 1) of the present invention monitors and handles the operation of the aspirate-dispense system 10 (FIG. 1), including the syringe pump 22 and dispenser 12, is discussed in detail now. It will be appreciated that the control system of the present invention may efficaciously be utilized with other liquid delivery systems, direct current fluid sources and dispensers.

Top Level Control and Underlying Physics

Figure 8:
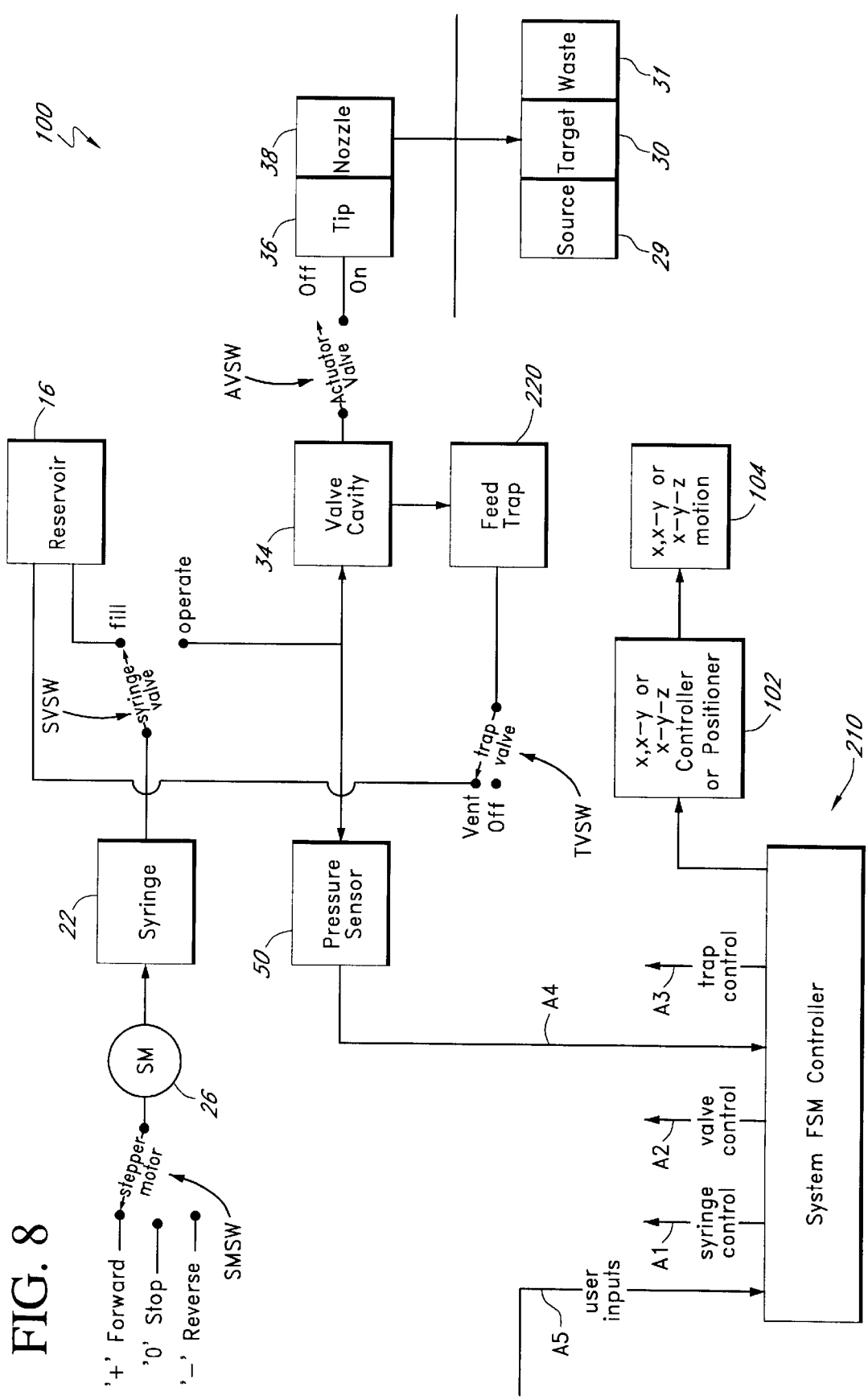
FIG. 8 is a simplified top-level control system (in block diagram format) schematically illustrating the operation of the aspirate-dispense system of FIG. 1 and having features in accordance with one preferred embodiment of the present invention.

FIG. 8 is a simplified top-level state-variable control system 100 (in block diagram format) which schematically illustrates the control and operation of a liquid delivery system, such as the positive displacement aspirate-dispense system 10 shown in FIG. 1, and has features in accordance with one preferred embodiment of the present invention. For clarity and convenience, the blocks of FIG. 8 are labeled with the same reference numerals as those used for any corresponding system elements or components of FIGS. 1–3.

The control system/diagram 100 (FIG. 8) shows block elements for the stepper motor 26, the syringe pump 22, the fluid reservoir 16, the valve cavity 34, the pressure sensor(s) 50, the tip 36, the nozzle 38, the bubble trap 220, the fluid source 29, the target 30, a waste position 31 and the system finite state machine (FSM) controller 210. The control system/diagram 100 also includes a stepper motor switch SMSW, a syringe valve switch SVSW, an actuator valve switch AVSW and a trap valve switch TVSW.

As schematically illustrated in FIG. 8, the controller 210 operates and controls the syringe pump 22 via actuations of the stepper motor switch SMSW and the syringe valve switch SVSW (this is represented by arrow A1 in FIG. 8). The controller 210 also operates and controls the drop-on-demand valve 20 via actuations of the actuator valve switch AVSW (this is represented by arrow A2 in FIG. 8). The controller 210 further operates and controls the bubble trap 220 via actuations of the trap valve switch TVSW (this is represented by arrow A3 in FIG. 8).

The controller 210 receives pressure data from the pressure sensor(s) 50 (this is represented by arrow A4 in FIG. 8). As discussed in greater detail later herein, the pressure data is used to derive various fluid and/or flow diagnostics. The controller also receives data input by the operator (this is represented by arrow A5 in FIG. 8).

The controller 210 controls the relative X, X-Y or X-Y-Z motion between various components or associated components of the aspirate-dispense system 10 (FIG. 1) such as between the source 29, target 30 and the drop-forming nozzle 38. This can be achieved by utilizing stepper motors and the like with the X, X-Y or X-Y-Z tables 212, 214 (FIG. 1) and is schematically represented by the block element 102 in FIG. 8. The resulting relative motion is represented by the block element 104 in FIG. 8.

Figure 9:
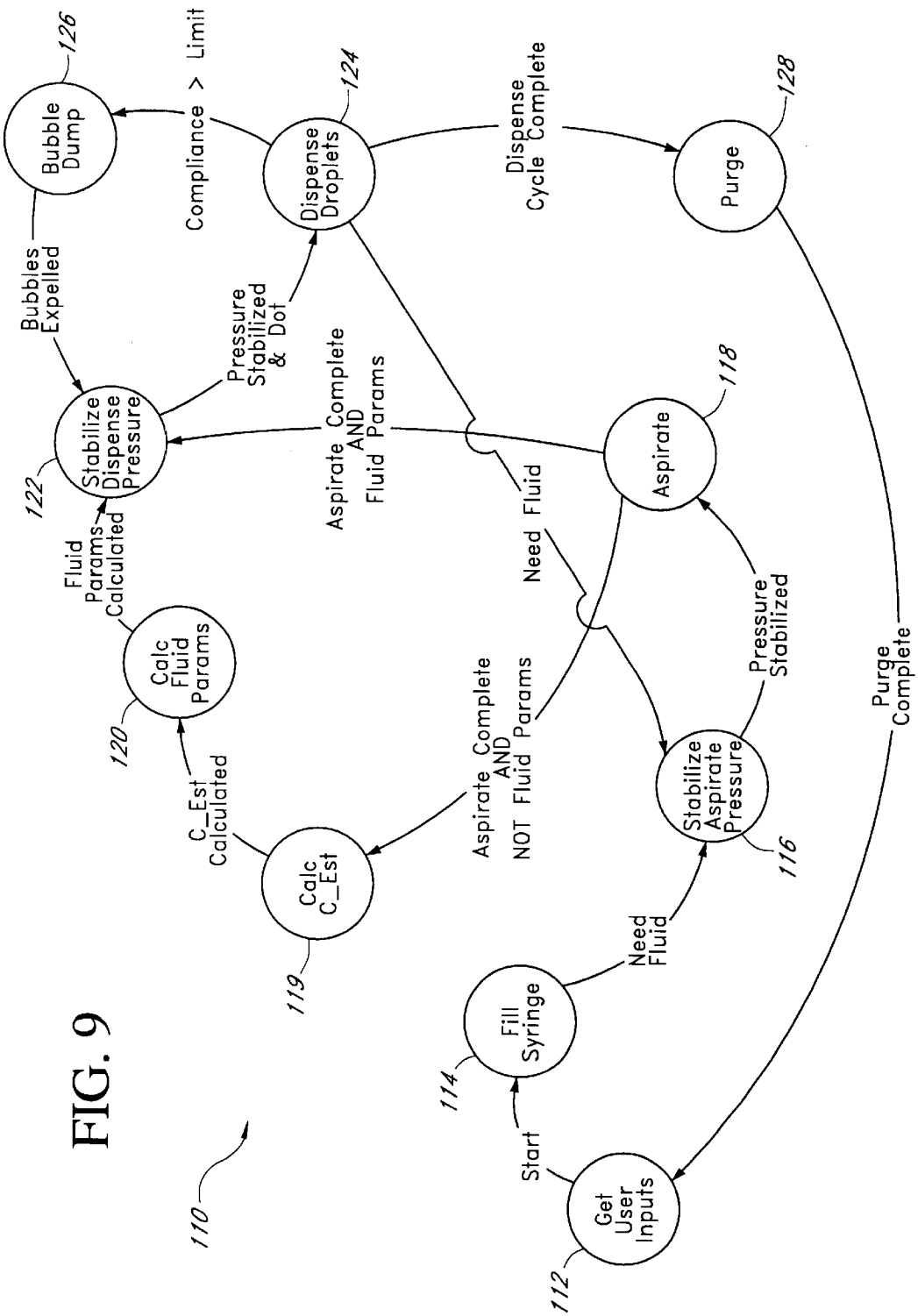
FIG. 9 is a simplified state diagram schematically illustrating the operation of the aspirate-dispense system of FIG. 1 and having features in accordance with one preferred embodiment of the present invention.

FIG. 9 is a simplified top-level state diagram 110 which is associated with the top-level control system/diagram 100 of FIG. 8 and schematically illustrates one preferred sequence, combination or cycle of steps or acts for controlling the operation of the aspirate-dispense system 10 (FIG. 1). The user or operator provides the inputs (as listed below) and the system hardware parameters (as listed below) are set, if needed, in step 112 and the system 10 is started. These inputs are used by the controller 210 to set, compute and/or estimate the operational parameters such as the valve actuation frequency, the valve on time, the stepper rate and flow rate(s), as needed or desired. These operational parameters can also be set, computed, estimated or adjusted at a later time. In step 114, the syringe pump 22 is filled with system fluid such as distilled water or other solvents. The system 10 now needs a fluid which is to be transferred. Prior to aspiration of the fluid, in step 116 the system pressure is stabilized or set to a predetermined and/or steady state aspirate pressure. Once the desired aspirate pressure is achieved, the fluid is aspirated in step 118. After aspiration, if the fluid parameters such as density and viscosity are not known then the system compliance is estimated, determined and/or computed in step 119. This value of the compliance in conjunction with other known parameters is used to estimate, determine and/or compute fluid parameters (such as, flow resistances, density and viscosity). If the density and viscosity of the fluid are already known, steps 119 and 120 can be skipped.

Prior to dispensing of the fluid onto the desired target, in step 122 the system pressure is stabilized or set to a predetermined and/or steady state dispense pressure. Once the dispense pressure is stabilized, the system 10 is then used to dispense droplets in step 124. During dispensing in step 124, the compliance of the system may increase to an undesirable level or limit due to bubble precipitation and accumulation. In this case, the bubbles are dumped or purged in step 126. Once the bubbles have been expelled, in step 122 the system pressure is again stabilized or set to a predetermined and/or steady state dispense pressure and dispensing commences in step 124.

If more fluid is needed to continue dispensing, the pressure is again stabilized or set to a predetermined and/or steady state aspirate pressure for aspirating in step 116. Once the desired aspirating pressure is achieved, the fluid is aspirated in step 118. After aspiration, if needed, the relevant parameters are estimated, computed and/or determined in steps 119 and 120. In step 122, the system pressure is stabilized or set to a predetermined and/or steady state dispense pressure for dispensing. Once the pressure is stabilized to the desired dispensing pressure, the system 10 is then used to dispense droplets in step 124.

Once the dispense cycle is complete, any remaining source fluid can be purged or flushed from the system 10 in step 128. Once the purge is complete, the system 10 is ready to start again at step 112, if needed. TABLE 1 below is a mode matrix of the top-level control and is useful in summarizing and clarifying the various operations as illustrated by the control system 100 of FIG. 8 and the state diagram 1 10 of FIG. 9.

TABLE 1

Mode Matrix of the Top-Level System of FIG. 8

| MODE | Stepper Motor Switch (SMSW) | Syringe Valve Switch (SVSW) | Trap Valve Switch (TVSW) | Actuator Valve Switch (AVSW) | X, X–Y or X–Y–Z Positioner |
|---|---|---|---|---|---|
| Fill Syringe | Reverse | Fill | Off | Off | X |
| Dispense Dot/Droplet | Forward | Operate | Off | Single or Multiple Pulse | Stationary over Target |
| Dispense Line or Spaced Dots/Droplets | Forward | Operate | Off | Multiple Pulse | Motion over Target |
| Aspirate | Reverse | Operate | Off | Multiple Pulse or 100% Duty Cycle | Source |
| Hold | Stop | Operate | Off | Off | X |
| Purge | Forward | Operate | Off | Multiple Pulse or 100% Duty Cycle | Waste |
| Stabilize Aspirate Pressure | Reverse | Operate | Off | Off | X |
| Dump Bubbles | Forward | Operate | Vent | Off | X |
| Calculate Fluid Parameters | X | X | Off | X | X |
| Stabilize Dispense Presssure | Forward | Operate | Off | Off | X |

Fill Syringe Mode

The "Fill Syringe" mode is used to draw system fluid 14 (FIG. 1) from the reservoir 16 into the syringe pump 22. The open-close valve 25a is opened and the stepper motor 26 is operated in the reverse direction to draw a predetermined quantity of system fluid 14. Once the desired quantity of system fluid 14 has been collected, the valve 25a is closed. Preferably, and to expedite the filling, the stepper motor 26 is operated at the maximum allowable speed, though alternatively slower speeds may be efficaciously utilized.

Dispense and Calculate Fluid Parameters Modes

During dispense modes the actuator valve 20 (FIG. 1) and the stepper motor 26 are provided pulse width and frequency commands from the system controller 210. The stepper motor 26 is operated in the forward direction with the open-close valve 25a in the closed position. One or more droplets can be dispensed at one location before proceeding to the next. The target 30 can comprise a glass slide, substrate, membrane or microtiter plate and the like. Typically, in the dispense line mode the drops are dispensed closer to one another as compared to the dispense dot/droplet mode. The following is a list of user inputs and hardware parameters that are provided to the system controller:

User Inputs:

Desired Droplet Size: Vd in liters

Fluid Density: $\rho$ in kg/m$^3$ (if known)

Fluid Viscosity: $\mu$ in Pa-sec (if known)

Fluid Surface Tension: $\sigma$ in N/m

System Hardware Parameters or Inputs (provided by user):

Motion Inputs or Parameters or Pattern, including:
Distance Between Drops: X_drop in meters (depends on application)
Translator or Table Velocity: U_xy in m/sec (can be varied)

Stepper volume per step: Vstep in liters

Stepper maximum step rate: Fstepmax in Hz

Valve minimum on time: Tv_min in sec

Nozzle diameter: D_nom in meters

Nozzle length: L_nom in meters

Nozzle Discharge Coefficient: Cd

Fluid Angle with Target or Substrate: $\theta$ in radians (if needed)

Valve Control Equations

The valve control is based on meeting a target, predetermined or preselected Weber number in the nozzle 38 so that proper drop detachment occurs. This is done as follows:

$$Qnom\_Nwe = \frac{\sqrt{2Nwe\_max\sigma/\rho}\ \pi(D\_nom/2)^{\frac{3}{2}}}{2} \quad (25)$$

$$Qest = \frac{Vd}{1000Tv\_min} \quad (26)$$

$$Vd\_min = 1000Qnom\_NweTv\_min \quad (27)$$

if, $Vd < Vd\_min$ $Q = Qest$, otherwise: $Q = Qnom\_Nwe$ (28)

$$Tv\_est = \frac{Vd}{1000Q} \quad (29)$$

if, $Tv\_est \leq Tv\_min$ $Tv = Tv\_min$, otherwise: $Tv = Tv\_est$ (30)

$$Fvalve = \frac{U\_xy}{X\_drop} \quad (31)$$

where, Qnom_Nwe is the nominal nozzle flow rate based on the target Weber number Nwe_max, Qest is the estimate of maximum nozzle flow rate for a given droplet volume Vd and the hardware parameter Tv_min, Vd_min is the minimum drop size based on Qnom_Nwe and Tv_min, Q is the nozzle flow rate, Tv_est is an estimate of the valve open or on time based on Q and the desired drop size Vd, Tv (pulse width) is the valve open or on time, and Fvalve is the valve open-close frequency. The target or preselected Weber number at the nozzle 38 is achieved unless the user requests too small of a drop size. A lower limit for the drop size can be determined empirically for a given production set up.

Stepper Control Equations

The stepper control is based on meeting the input volume requirements as follows:

$$Fstep = \frac{VdFvalve}{Vstep} \quad (32)$$

where, Fstep is the stepper step rate or frequency.

Nozzle Flow Parameter Estimates

1. Flow Resistance Parameters

The nozzle pressure or pressure drop at normal dispensing operating conditions can be estimated from the following:

$$Rc = \frac{8\mu L\_nom}{\pi\left(\frac{D\_nom}{2}\right)} \quad (33)$$

$$Ro = \frac{\sqrt{\frac{\rho}{2}}}{Cd\pi\left(\frac{D\_nom}{2}\right)^2} \quad (34)$$

$$Ps\_cap = QRc \quad (35)$$

$$Ps\_orf = (QRo)^2 \quad (36)$$

$$Ps\_in = Ps\_cap + Ps\_orf \quad (37)$$

where, Rc is the nozzle capillary flow resistance, Ro is the nozzle orifice flow resistance, Ps_cap is the pressure drop due to Rc, Ps_orf is the pressure drop due to Ro, Ps_in is the nozzle pressure drop, and Q is the nozzle flow rate. Since the bulk of the pressure drop during dispensing is through the system nozzle 38 (FIG. 3) due to the nozzle 38 being the major contributor to flow resistance, Ps_in is an estimate of the desired dispensing steady state pressure Pss.

2. Nozzle Parameters from Steady State Pressure Measurements

An estimate of the steady state pressure can also be obtained by estimating the nozzle capillary and orifice flow resistances by utilizing pressure measurements from the sensor(s) 50 during dispensing. The capillary flow resistance and the orifice flow resistance can be estimated by making two measurements of the system pressure at two flow rates during steady state dispensing from the following:

$$Rc\_est = \frac{PlQh^2 - PhQl^2}{QhQl(Qh - Ql)} \quad (38)$$

$$Ro\_est = \sqrt{\frac{PhQl - PlQh}{QhQl(Qh - Ql)}} \quad (39)$$

where, Ql is the low flow rate, Qh is the high flow rate, Pl is the pressure measurement at Ql, Ph is the pressure measurement at Qh, Rc_est is the estimate of the capillary flow resistance and Ro_est is the estimate of the orifice flow resistance. Note that Rc_est and Ro_est can desirably include contributions from the flow resistances of the tip 36, valve 20 and/or other resistances in the fluid flow path, though as indicated above these resistances are expected to be small compared to the nozzle flow resistance.

The two pressure measurements, Pl and Ph, can be made can be made during steady state on-line dispensing by modulating or perturbing the flow rate about the operating point by a small amount, for example, about ±5%. Optionally, a calibration mode can be used off-line to make the pressure measurements. Once estimates of the capillary flow resistance, Rc_est, and the orifice flow resistance, Ro_est, have been determined, these can be used as follows to obtain an estimate of the pressure drop which can be estimated as a steady state pressure Pss:

$$Pss = QRc\_est + (QRo\_est)^2 \quad (40)$$

Advantageously, the above estimates of the capillary flow resistance, Rc_est, and the orifice flow resistance, Ro_est, permit the density and viscosity of the fluid to be computed by using:

$$\mu\_est = \frac{\pi Rc\_est\left(\frac{D\_nom}{2}\right)^4}{8L\_nom} \qquad (41)$$

$$\rho\_est = 2\left(\pi Cd \frac{D\_nom^2}{4} Ro\_est\right)^2 \qquad (42)$$

where, $\rho\_est$ is the estimated fluid viscosity and $\mu\_test$ is the estimated fluid density.

3. Nozzle Parameters from Transient Pressure Measurements

Prior to steady state dispensing, transient pressure measurements utilizing the pressure sensor(s) 50 can be used to the estimate the capillary and orifice flow resistances. Again, desirably these flow resistances can include contributions from the flow resistances of the tip 36, valve 20 and/or other resistances in the fluid flow path, though as indicated above they are expected to be small compared to the nozzle flow resistance. The transient approach is generally accurate when the initial pressure is within about 30–50% of steady state value because a linearized approximation of the differential equations is used. The linearized pressure equations for an initial pressure of Po at the time that pulsed dispensing operation begins and decays to the steady state value of Pss can be approximated by:

$$P(t) = Pss + (Po - Pss)e^{-\frac{t}{\tau} FvalveTv} \qquad (43)$$

$$\tau = C\left(Rc + \frac{2Ro^2 Qstep}{FvalveTv}\right) \qquad (44)$$

$$Pss = Ro^2 Qnozzle^2 + RcQnozzle \qquad (45)$$

$$Qnozzle = \frac{Qstep}{FvalveTv} \qquad (46)$$

where, P(t) is the instantaneous pressure as a function of time t, $\tau$ is the system time constant, C is the elastic capacitance, Qstep is the flow rate provided by the stepper motor 26, and Qnozzle is the flow rate through the nozzle 38. The elastic capacitance, C, can be estimated from pressure and volume changes with the drop-on-demand valve 20 closed, as is discussed below. Note that (FvalveTv) is a scaling factor since the drop-on-demand valve 20 is not open all the time in pulsed dispensing operation. If the valve 20 is open continuously, this scaling factor reverts to 1 since the nozzle flow rate, Qnozzle, and the stepper flow rate, Qstep, are the same.

The above equations (43) to (46) can be manipulated to give:

$$\tau = \frac{t1}{\ln(|Po - Pss|) - \ln(|P1 - Pss|)} FvalveTv \qquad (47)$$

$$Rc = \frac{Fvalve}{Qstep}\left(2PssTv - \frac{Qstep\tau}{FvalveC\_Est}\right) \qquad (48)$$

$$Ro = \frac{Fvalve}{Qstep}\sqrt{\left(\frac{Qstep\tau}{C\_EstFvalve} - PssTv\right)Tv} \qquad (49)$$

where, Po is the measured initial pressure prior to pulsed dispensing at time to, Pss is the measured steady state pressure after a substantially long time tss, and P1 is the measured pressure during decay at an intermediate time t1. These pressures can be measured using the pressure sensor (s) 50. Several measurements of pressure/time can be made and the results averaged to reduce noise. In this manner estimates of the nozzle capillary flow resistance, Rc, and nozzle orifice flow resistance, Ro, are obtained. Note that Rc and Ro can desirably include contributions from the flow resistances of the tip 36, valve 20 and/or other resistances in the fluid flow path, though as indicated above these resistances are expected to be small compared to the nozzle flow resistance. Once estimates of the capillary flow resistance, Rc, and the orifice flow resistance, Ro, have been determined, these can be used as follows to obtain an estimate of the pressure drop which can be estimated as a steady state pressure Pss:

$$Pss = QRc + (QRo)^2 \qquad (50)$$

Advantageously, the above estimates of the capillary flow resistance, Rc, and the orifice flow resistance, Ro, permit the density $\rho$ and viscosity $\mu$ of the fluid to be computed by using:

$$\mu = \frac{\pi\left(\frac{D\_nom}{2}\right)^4 Rc}{8L\_nom} \qquad (51)$$

$$\rho = 2\left(Cd\pi\left(\frac{D - nom}{2}\right)^2 Ro\right)^2 \qquad (52)$$

Aspirate Mode

The "aspirate mode" is used to draw fluid from the source 29 into the system via the nozzle 38. The stepper motor 26 is operated in the reverse direction with the nozzle 38 dipped in the source fluid. The aspiration is preferably performed at a predetermined and/or steady state system pressure. Preferably, the aspirate pressure is at or less than zero, slightly negative or reduced relative to the ambient pressure level.

Preferably, the valve 20 is open continuously during aspiration, that is, a 100% duty cycle is utilized. Advantageously, since the system pressure is at or close to zero, predetermined small volumes of source fluid can be substantially accurately aspirated by metering the displacement of the syringe pump 22. Also, by preferably utilizing an optimally slow motion of the syringe pump plunger 64 (FIG. 2), via the stepper motor 26, while having the valve 20 fully open, the reduced/negative aspirate system pressure is kept close to zero so that the flow of source fluid into the nozzle 38 and tip 36 is maintained generally laminar. Moreover, utilizing a 100% valve duty cycle, during aspiration, further assists in maintaining a generally laminar flow of source fluid into the nozzle 38 and tip 36. Thus, turbulent mixing of source fluid with system fluid 14 (FIG. 1) is minimized.

In other preferred embodiments, the valve frequency, on time and/or duty cycle and the stepper motor speed can be selected in alternate manners with efficacy, as required or desired, giving due consideration to the goals of effectively aspirating source fluid, and/or of achieving one or more of the advantages and benefits as taught or suggested herein.

Hold Mode

"Hold mode" is a standby condition used while the system is waiting because of various reasons with the stepper motor 26 stopped. This may happen, for example, when the system is awaiting further instructions from the operator.

Purge Mode

The "purge mode" is used to flush the system. For example, this may be done at the termination of a dispense cycle to remove any residual aspirated fluid in the system prior to the aspiration of a new source fluid. During purging, the nozzle 38 is placed over a waste position or receptacle 31 (FIG. 8).

Normal Pressure Purge

In one preferred embodiment, the normal dispensing operating pressure is used while purging the system and the stepper motor 26 is operated in the forward direction. A larger than normal drop size can be selected by the user for the purge mode, for example, ten times the usual droplet size and the system operated in a droplet dispensing mode. Alternatively, a 100% valve duty cycle may be utilized, that is, the valve 20 is continuously open during the purging. The total amount of volume to be purged is also selected.

High Pressure Purge

In another preferred embodiment, the system is operated at a higher pressure than that used for normal dispensing operations. This can be accomplished by setting the stepper rate to two to three or more times the normal dispensing rate, thereby raising the pressure. The valve 20 may be pulsed or a 100% valve duty cycle utilized. The total amount of volume to be purged can also be selected.

Dump Bubbles Mode

When the elastic compliance within the system exceeds a certain level, the unwanted gaseous bubbles are expelled from the system by opening the bubble trap valve 225 (FIG. 1) preferably with the valve 20 closed. The bubble-infested fluid can be dumped into a waste position 31 (FIG. 8) or it can be returned to the reservoir 16.

Pressure Bleed

In one preferred embodiment, the trap valve 225 is opened and the pressure is left to bleed down to zero or ambient conditions by itself, thus reducing the fluid loss.

Pressure Pump

In another preferred embodiment, the trap valve 225 is opened and the syringe pump 22 (or stepper motor 26) is operated in the forward direction until a desired or predetermined volume of fluid is pumped out of the system. Alternatively, the system pressure is raised by operating the syringe pump 22 (or stepper motor 26) in the forward direction with the valve 225 initially closed. The valve 225 is then opened and the syringe pump 22 operated in the forward direction until a desired or predetermined volume of fluid is pumped out of the system. Alternatively, after the system has been pressurized, the pressure may be allowed to bleed down to zero or ambient conditions by itself. The pressurized bubble dump or purge technique is faster than the pressure bleed method and is generally more reliable in ensuring that all or most of the bubbles are expelled from the system.

Stabilize Pressure Mode

As indicated above, aspirate and dispense operations are preferably performed at a predetermined and/or steady state pressure. Thus, after purge, bubble dump, aspirate and dispense functions the pressure may need to be adjusted to the predetermined and/or steady state value prior to proceeding with aspiration or dispensing.

Set Pressure at Operating Point

Preferably, a pre-dispense pressure adjustment, compensation or correction involves displacing the syringe pump plunger 64 (FIG. 2), via the stepper motor 26, while maintaining the valve 20 in a closed position. The amount of plunger displacement can be computed from the elastic compliance and the steady state pressure. The steady state pressure, typically between 2000 to 6000 Pascals (Pa), can be estimated, as discussed above, from flow resistances and/or prior steady state or transient pressure measurements. The steady state pressure can also be estimated from previously formulated parametric tables or charts based on parameters such as the desired drop size and/or flow rate and nozzle dimensions, among other parameters. The elastic capacitance, C, can be estimated from:

$$C\_Est = \frac{\Delta V}{\Delta P} \tag{53}$$

where, $\Delta V$ is the change in volume as determined by the displacement of the syringe pump plunger 64 and $\Delta P$ is the change in pressure as measured by the pressure sensor(s) 50, with the valve 20 closed. Thus, the volume displacement, $\Delta V$, of the syringe pump plunger 64, as provided by the steps of the stepper motor 26, required to achieve steady state pressure conditions, Pss, can be estimated by using:

$$\Delta V = C\_Est(P - Pss) \tag{54}$$

where, P in equation (54) is the instantaneous pressure as measured by the pressure sensor(s) 50. By constantly or periodically monitoring the pressure, P, as the syringe pump plunger 64 is moved a continuous or periodic and updated measurement of the elastic compliance, C_Est, can be iteratively used in equation (54) until the system pressure converges to the steady state value.

Equation (54) can be similarly used to estimate the plunger displacement to provide pressure adjustment or compensation prior to an aspirate function. The plunger 64 is displaced to adjust or reduce the system pressure with the valve 20 in the closed position. In this case, and as discussed before, the desired aspirating pressure will typically be less than zero, slightly negative or less than the ambient pressure.

Advantageously, this technique of setting the aspirate and dispense pressure at the desired operating point does not waste valuable fluid or reagent since the valve 20 is closed. Moreover, the pressure adjustment can desirably be implemented quickly, since the plunger volume displacement has already been determined. This adds to optimizing the performance of the aspirate-dispense system 10.

Dispense Drops at Waste Container or Position

This involves dispensing a number of drops in a waste position while actuating the valve 20 and stepper motor 26 until the system pressure reaches or decays to a steady state value. Though this results in some wastage of fluid, the advantages are that the pressure/time data can be used to estimate the nozzle flow resistances (using equations (47) to (49)), the fluid viscosity and density (using equations (51) and (52)), and the elastic capacitance using the basic differential equation of the elastic compliance:

$$\frac{dP}{dt} = \frac{Q}{C} \tag{55}$$

where, Q is the nozzle or stepper flow rate and C is the elastic compliance.

Error Flags (Warnings)

The operation of the system is monitored and various error flags and warnings are provided to alert the system controller or the operator of possible undesirable operating conditions.

Flow Numbers

The nozzle or droplet exit velocity Unom is given by the following:

$$Unom = \frac{4Q}{\pi D\_nom^2} \quad (56)$$

The Reynolds number Re is given by the following:

$$Re = \frac{\rho D\_nom Unom}{\mu} \quad (57)$$

The Weber number We is given by the following:

$$We = \frac{\rho D\_nom Unom^2}{\sigma} \quad (58)$$

The Error Flags can include the following:
Laminar Flow Check
  If Re>2000:
    "Reynolds Number Too High; Turbulent Flow May Result"
Drop Detachment Check
  If We<1:
    "Weber Number Too Low; Unreliable Drop Detachment May Result"
High Pressure Check
  System pressure P is or will be greater than the feed line burst pressure Pmax (for example, P>60,000 Pa):
    "Operating Pressure Too High; Feed lines May Fail"
Splash Check
  Unom>Usplash:
    "Nozzle Velocity Too High; Splashing May Result"
  Usplash is the splash velocity and can be estimated by the following equation (59):

$$Usplash = \frac{\sqrt{-3CDK\rho\sigma\cos\theta + \alpha^2 C^9 K^2 \mu^2 + 3C^3 DK\rho\sigma - 12CD\rho\sigma + 12DK\rho\sigma}}{\sqrt{C} D\rho} + \frac{\alpha C^4 K \mu}{D\rho}$$

where, C defines the maximum diameter of the drop on the surface when a splash occurs relative to the spherical drop diameter before impact, K is the total energy multiple required for a splash to occur, D is nozzle diameter and α is a constant that expresses the uncertainty in the viscous power loss (see *Modeling Axisymmetric Flows: Dynamics of Films, Jets and Drops*, Stanley Middleman, 1995, Academic Press, Page 185, incorporated by reference herein).
Valve Frequency Check
  If Fvalve>1/Tv:
    "Valve Frequency Too High; Cannot Produce Correct Drop Size"
Stepper Resolution Check
  If Fstep>KFvalve, where K=2 or more:
    "Stepper Volume Per Step Is Too High; Incorrect Drop Size May Result"
Stepper Rate Check
  If Fstep>Fstepmax:
    "Stepper Frequency Too High; Syringe Can Not Supply Required Flow Rate"

Elastic Compliance
  If C>Cmax (upper limit of allowable capacitance):
    "Elastic Compliance Too Large; Time To Vent Bubbles"
  Note that the elastic capacitance can be estimated from equations (53) and/or (55). The elastic capacitance and/or changes in elastic capacitance can also be inferred from observing the measured pressure and/or pressure profiles during pulsed dispensing. The maximum difference in the instantaneous pressure measurements (ΔPmax) during pulsed operation will decrease as the system capacitance increases and this may be used to infer or estimate the elastic capacitance and/or changes in the elastic capacitance.

Synchronization

The actuations of the stepper motor 26, translator 214 (and translator 212) and the valve 20 are synchronized to avoid errors. The synchronization can utilize coincident start and stop or predetermined phase lags or leads.
Stepper-Valve Timing Improper stepper motor-valve synchronization can cause undesirable changes in pressure. These can be estimated from the basic differential equation (55) of the elastic compliance. For a nominal stepper flow rate of about $5 \times 10^{-10}$ m³/sec and an elastic compliance of about $1 \times 10^{-14}$ m⁵/N, the pressure slew rate will be about 50,000 Pa/sec. For a pressure change or error of about 250 Pa, the timing error is about 5 milliseconds. Note that higher values of the elastic compliance aid in reducing the pressure slew rate, however, it takes longer for the error to settle with higher values of compliance. Alternatively, stepper-valve actuations can utilize predetermined phase lags or leads, as needed or desired, giving due consideration to the goals of achieving one or more of the benefits and advantages as taught or suggested herein Valve-Translator Timing The translator is preferably allowed a time lead in order to allow for it to accelerate up to the operating velocity. Once the translator reaches the desired velocity, the valve can be actuated. An error in synchronizing the valve-translator will result in an position error at the dispensing location. If a position error of 10% is tolerable on an dot pitch of 2–3 mm with a maximum velocity of 1 m/sec, then the maximum timing error between the valve and the translator should be less than 0.25 milliseconds. Phase lags and/or leads can be provided, as needed or desired, for example; to compensate for the probable or anticipated trajectory of the droplets.

State Finite System Machine (FSM) Controller

Figure 10:
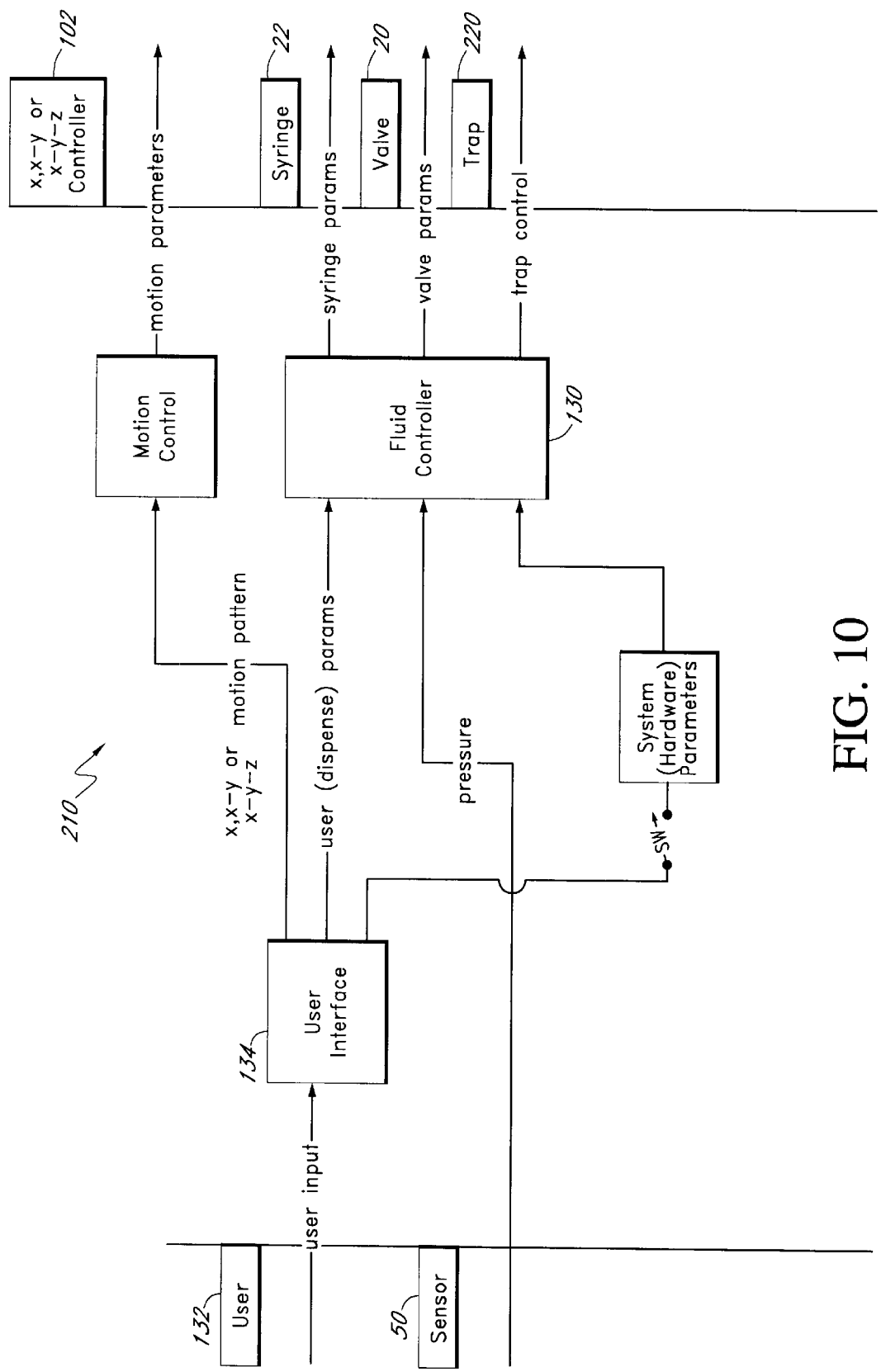
FIG. 10 is a simplified schematic of a finite state machine controller or control system (in block diagram format) having features in accordance with one preferred embodiment of the present invention.

FIG. 10 is a simplified schematic of a finite state machine controller or control system 210 (in block diagram format) having features in accordance with one preferred embodiment of the present invention. The controller 210 generally comprises a fluid controller or control system 130, the X, X-Y or X-Y-Z motion controller 102 and a user interface 134 (as discussed above).

The controller 210 receives inputs from a user 132 via the user interface 134. The inputs including the system hardware parameters are provided, communicated or transferred to the fluid controller 130. These inputs (and parameters) include the desired drop volume, the fluid density (if known), the fluid viscosity (if known), the fluid surface tension, the motion parameters or pattern including the distance between drops and the carriage velocity, the stepper volume per step, the stepper maximum step rate, the valve minimum on time, the nominal nozzle diameter, the nominal nozzle length, the nozzle discharge coefficient and the fluid angle with the target or substrate.

The user interface 134 also permits the user or operator 132 to select the mode of operation (aspirate mode, dispense mode and other modes, as described above) which is communicated to the controller 130. One or more of the pressure sensors 50 provide, communicate or transfer pressure data to the controller 130.

The controller 130 processes the information it receives and uses the processed information or output to control the operation of the syringe pump 22 (via the stepper motor 26), the drop-on-demand valve 20 and the bubble trap 220. This is done by providing electrical signals having length and duration to the pump stepper motor 26, the drop-on-demand valve 20, the syringe valve 25a (FIG. 1), and the bubble trap valve 225 (FIG. 1).

The operating parameters provided to the stepper motor 26 by the controller 130 include the stepper operating step rate and mode of operation. The operating parameters provided by the controller 130 to the drop-on-demand valve 20 include the valve on or open time, the valve open frequency and/or the valve duty cycle. Open-close commands are provided by the controller 130 to the syringe valve 25a and the bubble trap valve 225.

The motion parameters or pattern including the distance between drops and the carriage velocity are also provided, communicated or transferred to the X, X-Y or X-Y-Z motion controller 102. The mode of operation (aspirate mode, dispense mode and other modes, as described above) is also communicated to the motion controller 130. As indicated above, the controller 102 provides relative motion between the system nozzle 38 and the fluid source 29, fluid target 30 and waste position 31, and/or other components or associated components of the aspirate-dispense system 10, as needed or desired.

State-Variable Fluid Controller

Figure 11:
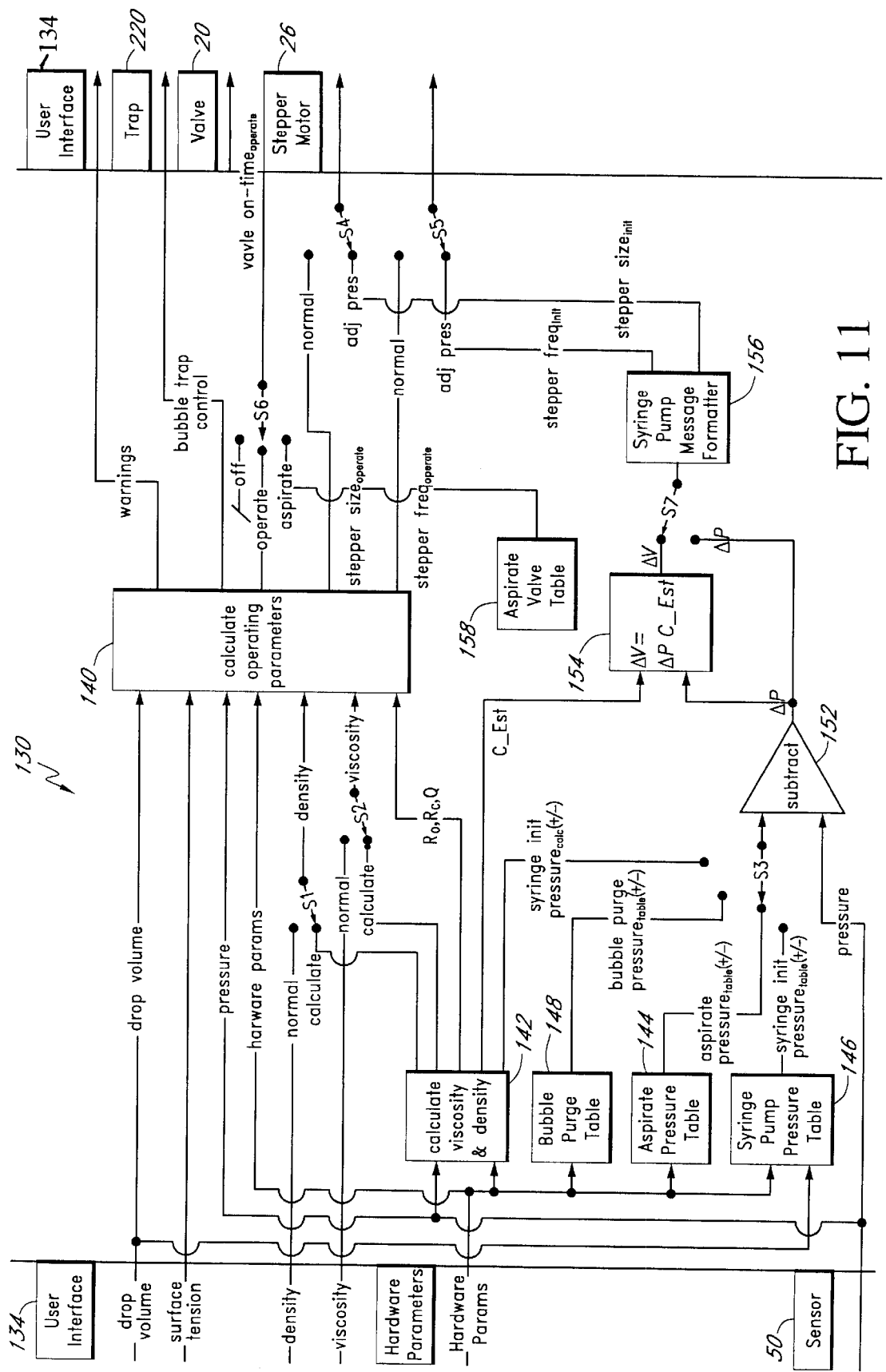
FIG. 11 is a simplified schematic of a state-variable fluid controller or control system (in block diagram format) of the finite state machine controller of FIG. 10 having features in accordance with one preferred embodiment of the present invention.

FIG. 11 is a schematic (in block diagram format) of the state-variable fluid controller or control system 130 having features in accordance with one preferred embodiment of the present invention. The control system 130 generally comprises a control block or system element 140 for calculating operating parameters, a control block or system element 142 for calculating or estimating fluid parameters (density and viscosity) and the system elastic capacitance, a control block or system element 144 for providing an estimate of the target and/or desired aspirate system pressure, a control block or system element 146 for providing an estimate of the target and/or desired dispense system pressure, a control block or system element 148 for providing an estimate of the target and/or desired dispense system pressure prior to or during the bubble dump/purge function.

The state-variable fluid controller 130 also comprises a subtracter system element 152 for comparing and computing the difference between the desired and/or target pressure and the actual system pressure as measured by the pressure sensor(s) 50. The subtract system element 152 feeds the pressure difference ($\Delta P$) output into a control block or system element (syringe pump message formatter) 156 either directly or via a control block or system element 154. The control block or system element 154 computes the volume change or displacement ($\Delta V$) that should be provided by the stepper motor 26 (or syringe pump 22). The control block or system element 156 then processes the pressure or volume input data and provides the stepper motor 26 with stepper frequency and stepper size commands to effectuate the pressure adjustment, correction or compensation. A further control block or system element (aspirate valve table) 158 is provided to control the on-time and/or duty cycle of the valve 20 during aspiration.

The control block or system element 140 receives input data including hardware parameters from the user. These inputs (and parameters) include the desired drop volume, the fluid density (if known), the fluid viscosity (if known), the fluid surface tension, the motion parameters or pattern including the distance between drops and the carriage velocity, the stepper volume per step, the stepper maximum step rate, the valve minimum on time, the nominal nozzle diameter, the nominal nozzle length, the nozzle discharge coefficient, and the fluid angle with the target or substrate.

If the fluid density and viscosity are not known, they can be estimated by the fluid parameter control block or system element 142, as discussed below, and provided to the control block or system element 140. If the fluid surface tension is not known, an off-line calibration can be used to estimate the surface tension, as discussed below, and provided to the control block or system element 140.

The control block or system element 140 further receives system pressure data as measured by the pressure sensor(s) 50. The system operator also communicates the mode of operation (aspirate, dispense, bubble dump and other modes, as discussed above) to the control block or system element 140 and/or to the control block or system elements 142, 144, 146, 148. If needed or desired, other data, if and when available, such as the flow resistances, flow rates and elastic capacitance can be provided to the control block or system element 140.

The control block or system element 140 processes the input data and controls the operation of the drop-on-demand valve 20 and the stepper motor 26 (and hence the syringe pump 22). The valve and stepper control equations (25) to (32) are used, and the control block or system element 140 provides command signals to control the valve on or open time, the valve open frequency and/or the valve duty cycle, and the stepper frequency or step rate and the stepper step size.

The control block or system element 140 also controls the operation of the bubble trap 220 via the valve 225 (FIG. 1) by opening the valve 225 when bubbles within the system are to be expelled. Furthermore, the control block or system element 140 continuously or periodically monitors and/or computes the Reynolds number, the Weber number, the nozzle velocity, the system pressure, the valve frequency, the stepper resolution, the stepper rate and the system elastic compliance and provides the system controller or user with warning signals or error flags (as discussed above) of any undesirable operational conditions. This can be done by providing an alert message via the user interface and/or by an audible alarm, among other ways.

TABLE 2 below is a top-level mode matrix of the fluid controller 130 and summarizes and clarifies some of the various operations as illustrated in FIG. 11 via the positions of the switches S1, S2, S3, S4, S5, S6 and S7. (The "adj pres" switch position in TABLE 2 and FIG. 11 refers to adjust pressure; the "purge" switch position in TABLE 2 refers to the "bubble purge pressure$_{table}$(±/−)" switch position in FIG. 11.)

TABLE 2

Mode Matrix of the Fluid Controller of FIG. 11

| MODE | S1 | S2 | S3 | S4 | S5 | S6 | S7 |
|---|---|---|---|---|---|---|---|
| Hold | normal | normal | X | operate (normal) | operate (normal) | off | X |
| Aspirate | X | X | X | adj pres | adj pres | X | X |
| Dispense | X | X | X | X | X | X | X |
| Bubble Purge or Dump | X | X | purge | adj pres | adj pres | off | ΔV |

Aspirate

TABLE 3 below is a mode matrix illustrating the aspirate sub-operations of the fluid controller 130 and summarizes and clarifies some of the various operations as illustrated in FIG. 11 via the positions of the switches S1, S2, S3, S4; S5, S6 and S7. (The "adj pres" switch position in TABLE 3 and FIG. 11 refers to adjust pressure; the "aspirate" switch position in TABLE 3 refers to the "aspirate pressure$_{table}$ (+/−)" switch position in FIG. 11.)

TABLE 3

Aspirate Submodes of the Fluid Controller of FIG. 11

| MODE | S1 | S2 | S3 | S4 | S5 | S6 | S7 |
|---|---|---|---|---|---|---|---|
| Initialize (Stabilize) Aspirate Pressure | X | X | aspirate | adj pres | adj pres | off | ΔV |
| Input Fluid (Aspirate) | X | X | aspirate | adj pres | adj pres | aspirate | ΔP |

Prior to aspiration of source fluid the system pressure is initialized, stabilized or set to a predetermined and/or steady-state aspirate pressure. The desired aspirate pressure is preferably less than zero, slightly negative or reduced relative to the ambient pressure value. The control block or system element 144 (aspirate pressure table) provides this aspirate pressure. The aspirate pressure can depend on the hardware parameters (for example, the nozzle and tip dimensions), the fluid parameters (for example, density and viscosity) and other parameters such as operational parameters. Some or all of these parameters can be provided to the control block or system element 144 which then outputs the aspirate pressure value. Alternatively, or in addition, the aspirate pressure may be predetermined for a given production set-up.

With the valve 20 closed, the subtract system element 152 computes the difference between the pressure output value from the control block or system element 144 and the system pressure as measured by the pressure sensor(s) 50. The pressure difference ΔP is provided to the control block or system element 154 which continuously or periodically computes the needed volume displacement of the syringe pump 22 using equation (54) or ΔV=C_EstΔP and provides this information to the control block or system element 156. The control block or system element 156 in turn communicates stepper frequency (and stepper size) commands to operate the stepper motor 26 to achieve the desired aspirate pressure. The elastic capacitance C_Est can be iteratively calculated during the pressure adjustment, correction or compensation using updated pressure measurements which desirably provides feedback control. Alternatively, the value of the elastic capacitance C_Est can be provided from the control block or system element 142.

Once the desired predetermined and/or steady state aspirate pressure is reached, the system is ready to proceed with aspiration of source fluid. Advantageously, the control system of the present invention allows the desired aspirate pressure to be reached quickly and without or with minimal wastage or leakage of any remaining source or system fluid from the system nozzle 38 since the valve 20 is closed during the pressure adjustment procedure. Desirably, this adds to the optimizing and efficiency of the operation of the aspirate-dispense system of the present invention.

During aspiration, the nozzle 38 is dipped in the fluid source 29 and the stepper motor 26 (and syringe pump 22) are operated in reverse or decremented to suck a precise and/or predetermined quantity of source fluid. The control block or system element 156 communicates stepper frequency (and stepper step size) commands to the stepper motor 26. The valve 20 is provided with commands from the control block or system element (aspirate valve table) 158 to operate the valve 20 at a predetermined valve on or open time, valve open frequency and/or duty cycle. In one preferred embodiment, a 100% valve duty cycle is utilized, though in other embodiments alternate duty cycles, on times and/or open frequencies can be utilized with equivalent efficacy, as required or desired, giving due consideration to the goals of achieving one or more of the advantages or benefits as taught or suggested herein.

Advantageously, during aspiration the subtract system element 152 computes or compares the difference between the desired predetermined and/or steady state aspirate pressure and the system pressure as measured by the pressure sensor(s) 50, and communicates this information to the control block or system element 156. If this pressure difference ΔP exceeds a certain tolerance limit, the control block or system element 156 adjusts the stepper frequency (and/or stepper step size) accordingly to maintain the system pressure substantially the same as the desired aspirate pressure. Desirably, this feedback control (loop) ensures that the aspiration is performed at substantially the desired predetermined and/or steady state pressure.

Dispense

TABLE 4 below is a mode matrix illustrating the dispense sub-operations of the fluid controller 130 and summarizes and clarifies some of the various operations as illustrated in FIG. 11 via the positions of the switches S1, S2, S3, S4, S5, S6 and S7. (The "adj pres" switch position in TABLE 4 and FIG. 11 refers to adjust pressure; the "calc" switch position in TABLE 4 refers to the "syringe init pressure $_{calc}$(+/−)" switch position in FIG. 11; the "init" switch position in TABLE 4 refers to the "syringe init pressure$_{table}$(+/−)" switch position in FIG. 11)

TABLE 4

Dispense Submodes of the Fluid Controller of FIG. 11

| MODE | S1 | S2 | S3 | S4 | S5 | S6 | S7 |
|---|---|---|---|---|---|---|---|
| Calculate C_Est | calculate | calculate | calc | adj pres | adj pres | off | ΔP |
| Calculate Fluid Parameters | calculate | calculate | X | normal | normal | operate | X |
| Initialize (Stabilize) Dispense Pressure | X | X | init | adj pres | adj pres | off | ΔV |
| Output Drops/Fluid (Dispense) | normal | normal | X | normal | normal | operate | X |

The "calculate C_Est" and "calculate fluid parameters" modes are used when the fluid parameters (density and viscosity) are unknown and need to be estimated experimentally. The "calculate C_Est" and "calculate fluid parameters" modes or operations are discussed in greater detail later herein.

Prior to dispensing of fluid onto or into the target 30, the system pressure is initialized, stabilized or set to a predetermined and/or steady-state dispense pressure. The control block or system element (syringe pump pressure table) 146 provides this dispense pressure. The control block or system element 146 can determine this desired dispense pressure in a number of ways. The desired drop volume and the system hardware parameters (including nozzle dimensions) are communicated to the control block or system element 146. Other parameters such as fluid parameters (density, viscosity), system parameters (flow resistances, elastic capacitance), flow parameters (flow rates, fluid exit velocity through the nozzle) and operational parameters (valve on time and frequency and/or valve duty cycle, stepper frequency and step size) can also affect the selection of the desired dispense pressure. Some or all of these parameters, as available or estimated, can be communicated to the control block or system element 146 to facilitate in the proper selection of the dispense pressure.

The desired steady state dispense pressure can be estimated, as discussed above, from flow resistances and/or prior steady state pressure measurements or transient pressure measurements. The steady state pressure can also be estimated from previously formulated parametric tables or charts based on some or all of the above fluid, system, flow and operational parameters. The control block or system element 146 can also utilize regression analysis techniques to estimate the optimum dispense pressure. Alternatively, or in addition, the dispense pressure may be predetermined for a given production set-up.

With the valve 20 closed, the control block or system element 146 communicates the desired dispense pressure to the subtracter 152. The subtract system element 152 computes the difference between the pressure output value from the control block or system element 146 and the system pressure as measured by the pressure sensor(s) 50. The pressure difference ΔP is provided to the control block or system element 154 which continuously or periodically computes the needed volume displacement of the syringe pump 22 using equation (54) or ΔV=C_EstΔP and provides this information to the control block or system element 156. The control block or system element 156 in turn communicates stepper frequency (and stepper size) commands to operate the stepper motor 26 to achieve the desired dispense pressure. The elastic capacitance C_Est can be iteratively calculated during the pressure adjustment, correction or compensation using updated pressure measurements which desirably provides feedback control. Alternatively, the value of the elastic capacitance C_Est can be provided from the control block or system element 142.

Once the desired predetermined and/or steady state dispense pressure is reached, the system is ready to proceed with dispensing onto or into the target 30. Advantageously, the control system of the present invention allows the desired dispense pressure to be reached quickly and without or with minimal wastage or leakage of any source and system fluid from the system nozzle 38 since the valve 20 is closed during the pressure adjustment procedure. Desirably, this adds to the optimizing and efficiency of the operation of the aspirate-dispense system of the present invention.

During dispensing, the nozzle 38 is positioned over the target 30 and the stepper motor 26 (and syringe pump 22) are incremented or operated in the forward direction to meter precise and/or predetermined quantities or volumes and/or flow rates of fluid via the nozzle 38 onto or into the target 30. The control block or system element 140 communicates stepper frequency (and stepper step size) commands to the stepper motor 26. The valve 20 is also provided with commands from the control block or system element 140 to operate the valve 20 at a predetermined valve on or open time, valve open frequency and/or duty cycle. Relative motion may be provided between the target 30 and the nozzle 38, as needed or desired, by the motion controller 102.

During dispensing, the pressure is monitored by the pressure sensor(s) 50 and communicated to the control block or system element 140. Changes in the measured pressure and/or pressure profile during pulsed dispensing operation can indicate a change in the system elastic capacitance due to gaseous bubble precipitation and accumulation. These changes in the measured pressure and/or pressure profile can be used to estimate and monitor the elastic compliance. Alternatively, or in addition, the differential equation (55) may be used to estimate the elastic compliance. Also, dispensing may be temporarily halted and the elastic compliance estimated using equation (53).

The updated value of the elastic compliance is communicated to the control block or system element 146 and an updated estimate obtained for the desired dispense pressure. The system pressure can then be adjusted to the desired dispense pressure by adjusting the actuations of the valve 20 and or stepper motor 26 without halting dispensing. Alternatively, dispensing may be temporarily halted, for example, if a significant pressure adjustment is needed, and the system pressure stabilized to the predetermined and/or steady state pressure as described above via the control block or system elements 152, 154, 156. Moreover, the system pressure is adjusted, as needed or desired, between dispense cycles. This feedback control desirably adds to the efficiency of the aspirate-dispense system of the present invention. A similar approach may be utilized if transient behavior is observed for other fluid, flow or system parameters.

The determination of the desired optimum dispense steady state pressure by the control system of the present invention advantageously results in accurate and repeatable performance, for example, in substantially consistently achieving the desired output, droplet size, flow rate and/or droplet exit velocity. The adjustment to the operating pressure to compensate for variations in the fluid, flow and/or operational characteristics of the system further enhances the repeatability and accuracy of the system.

Advantageously, the control system of the present invention adds to the versatility of the system and allows the rapid dispensing of droplets of different size. The control system can quickly adjust the system pressure to achieve the desired predetermined and/or steady state dispense pressure to change the ejected droplet size. Alternatively, or in addition, other system and operational parameters can be quickly adjusted to facilitate the rapid dispensing of droplets of different size. This can have various applications, for example, in performing a dilution series across one or more microtiter plates. The adaptability in quickly dispensing microfluidic droplets of different size can also be used in ink jet printing to produce high resolution halftone printed images.

The control system of the present invention also permits efficient operation to achieve varying desired flow or output characteristics. For instance, the system pressure and/or other system and operational parameters can be quickly adjusted to achieve a desired droplet velocity while maintaining the same droplet size. Typically, a lower output fluid velocity is preferred when dispensing on a glass slide to avoid splashing compared to dispensing in a microtiter plate wherein splashing is generally not a concern. Thus, the control system permits reliable operation at multiple system pressures to produce substantially the same fluid output and, in effect, can operate at forced, quasi or pseudo steady state and non-steady state pressures. This further adds to the versatility and adaptability of the control system of the present invention.

Bubble Purge or Dump

As discussed above, the bubble purge or dump mode can be performed in a number of ways. In one embodiment of the invention, prior to a bubble purge or dump procedure, the system pressure is initialized, stabilized or set to a predetermined pressure. The control block or system element (bubble purge table) 148 provides this predetermined pressure. This predetermined pressure can be dependent on the volume of fluid that is to be removed and/or the speed of the procedure. With the valves 20 and 225 closed, the control block or system element 148 communicates the desired predetermined pressure to the subtracter 152. The subtract system element 152 computes the difference between the pressure output value from the control block or system element 148 and the system pressure as measured by the pressure sensor(s) 50. The pressure difference $\Delta P$ is provided to the control block or system element 154 which continuously or periodically computes the needed volume displacement of the syringe pump 22 using equation (54) or $\Delta V = C\_Est \Delta P$ and provides this information to the control block or system element 156. The control block or system element 156 in turn communicates stepper frequency (and stepper size) commands to operate the stepper motor 26 to achieve the desired predetermined pressure. The elastic capacitance C_Est can be iteratively calculated during the pressure adjustment, correction or compensation using updated pressure measurements which desirably provides feedback control. Alternatively, the value of the elastic capacitance C_Est can be provided from the control block or system element 142.

Once the desired predetermined pressure is reached, the bubble trap valve 225 (FIG. 1) is opened and the fluid containing bubbles is expelled from the system. During this bubble expulsion, the stepper motor 26 can be operated in the forward direction to expedite the bubble removal procedure. Alternatively, the system pressure can be allowed to bleed down to zero or ambient pressure conditions by itself via the open bubble trap valve 225.

The high pressure bubble purge can also be performed via the system nozzle 38 with the valve 20 continuously open or pulsed. Similar pressurization procedures, as described for the bubble purge or dump mode, can be also be used to purge or flush the system of any residual or remaining aspirated fluid (or other fluid) through the system nozzle 38.

Calculate C_Est and Fluid Parameters

Density and Viscosity

Figure 12:
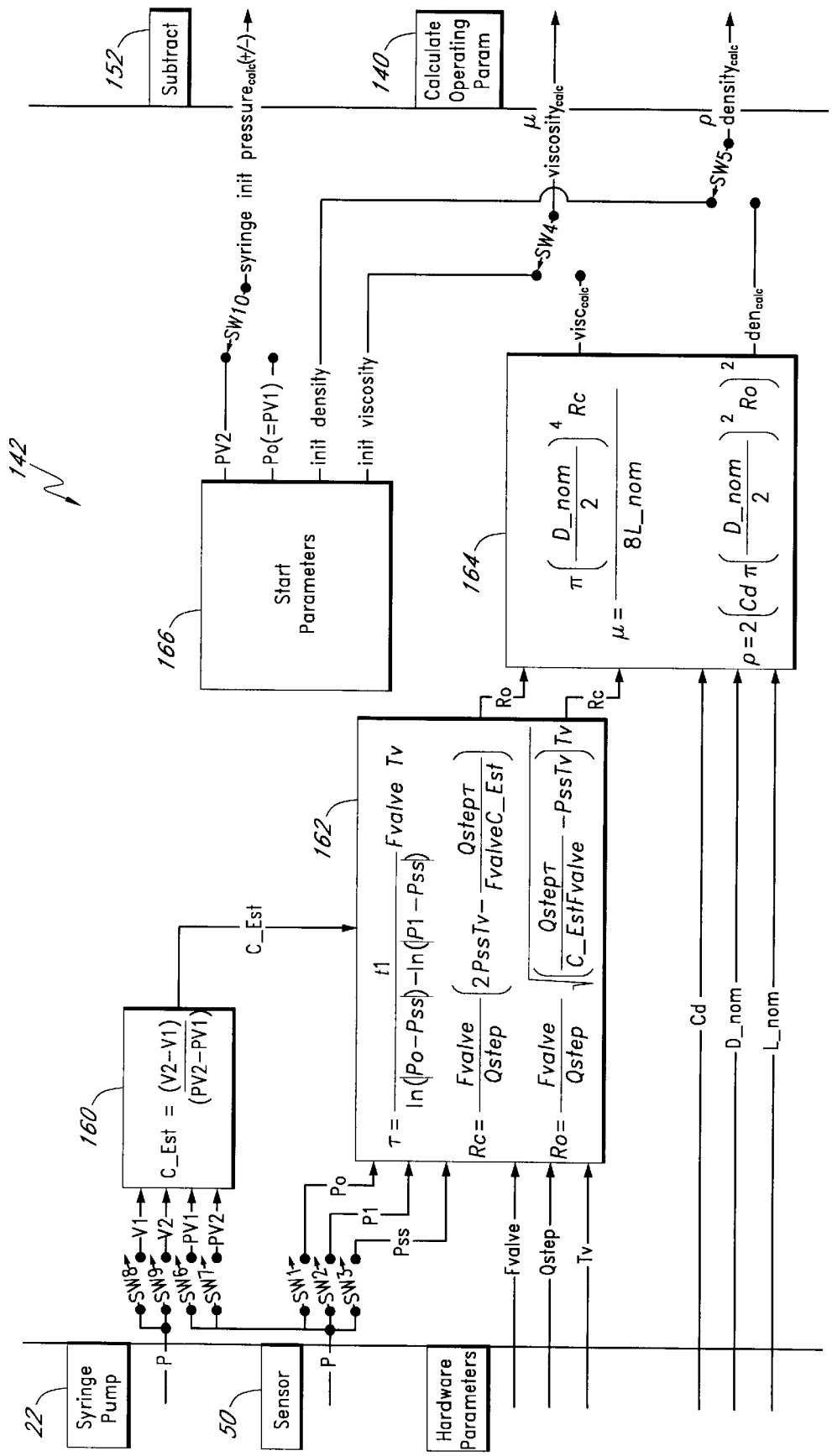
FIG. 12 is a detailed. schematic of a fluid parameter calculator (in block diagram format) of the fluid controller of FIG. 11 having features in accordance with one preferred embodiment of the present invention.
Figure 13:
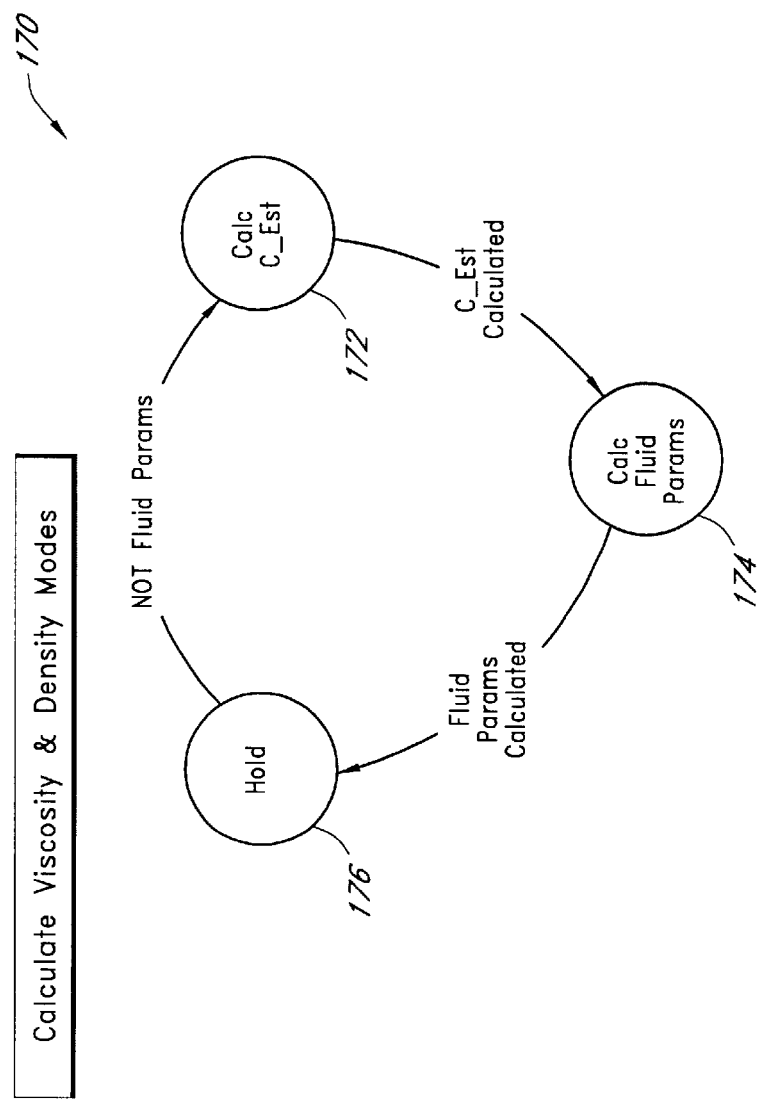
FIG. 13 is a simplified state diagram schematically illustrating the operation of the fluid parameter calculator of FIG. 12 having features in accordance with one preferred embodiment of the present invention.

Referring to FIGS. 12 and 13, if the fluid density and/or fluid viscosity are not known, the control block or system element 142 calculates or estimates the density and/or viscosity. As discussed above, this can be done from steady state pressure measurements (using equations (38)–(39) and (41)–(42)) or from transient pressure measurements (using equations (47)–(49) and (51)–(52)). These estimates of the density and viscosity are communicated to the control block or system element 140 (and 146).

FIG. 12 is a schematic of the fluid parameter calculator 142 (in block diagram format) which utilizes transient pressure measurements to estimate or determine the fluid density and/or viscosity and has features in accordance with one preferred embodiment of the present invention. The fluid parameter calculator 142 generally comprises a control block or system element 160 for calculating or estimating the system elastic capacitance, a control block or system element 162 for calculating or estimating the flow resistances, a control block or system element 164 for computing or estimating the fluid density and/or viscosity, and an initializer control block or system element 166.

If the system elastic compliance C_Est is not known, it has to be estimated or determined prior to computing the density and viscosity. TABLE 5 below is a mode matrix illustrating the Calculate C_Est dispense submode (represented by the control block or system element 160 in FIG. 12) and summarizes and clarifies some of the various operations as illustrated in FIG. 12 via the positions of the switches SW1, SW2, SW3, SW4, SW5, SW6, SW7, SW8, SW9 and SW10. Note that all inputs in TABLE 5 are sample and hold, and the values are read when the switches open. (The "init" switch position in TABLE 5 refers to corresponding "init density" and "init viscosity" switch positions in FIG. 12 which respectively represent the initial or user input density and viscosity.)

TABLE 5

Mode Matrix of the Calculate C_Est Dispense Submode of FIG. 12

| MODE | SW1 | SW2 | SW3 | SW4 | SW5 | SW6 | SW7 | SW8 | SW9 | SW10 |
|---|---|---|---|---|---|---|---|---|---|---|
| Start Calculations | closed | closed | closed | init | init | closed | closed | closed | closed | Po |
| Measure PV1 | closed | closed | closed | init | init | open | closed | open | closed | PV2 |
| Measure PV2 | closed | closed | closed | init | init | open | open | open | open | Po |

In the Calculate C_Est dispense submode, the initial system pressure Po=PV1 is measured by the pressure sensor (s) 50 and communicated to the control block or system element 160. A corresponding reference volume V1 is also communicated to the control block or system element 160. The valve 20 is closed during the Calculate C_Est dispense submode.

A predetermined pressure PV2 that is to be achieved within the system is then communicated to the subtract system element 152. The subtract system element 152 computes the difference between the pressure output value from the control block or system element 142 and the system pressure as measured by the pressure sensor(s) 50. The pressure difference ΔP is provided to the control block or system element 154 which computes the volume displacement of the syringe pump 22 to achieve PV2 using equation (54) or ΔV=C_EstΔP, based on a guess or estimate of C_Est, and provides this information to the control block or system element 156. The control block or system element 156 in turn communicates stepper frequency (and stepper size) commands to operate the stepper motor 26 to achieve the pressure PV2. The elastic capacitance C_Est is iteratively calculated during the pressure adjustment procedure by the control block or system element 154.

Once the pressure PV2 is reached, the pressure PV2 and the updated reference volume V2 is communicated to the control block or system element 160. The control block or system element 160 then computes the elastic capacitance by the expression C_Est=ΔV/ΔP=(V2−V1)/(PV2−PV1). An iterative technique can also be utilized for determining C_Est based on using updated and continuous or periodic pressure readings and volumes. This completes the Calculate C_Est dispense submode.

The system pressure is now reset to the initial pressure Po to initiate the Calculate Fluid Parameters dispense submode. TABLE 6 below is a mode matrix illustrating the Calculate Fluid Parameters dispense submode (represented by the control block or system elements 160, 162 in FIG. 12) and summarizes and clarifies some of the various operations as illustrated in FIG. 12 via the positions of the switches SW1, SW2, SW3, SW4, SW5, SW6, SW7, SW8, SW9 and SW10. Note that all inputs in TABLE 6 are sample and hold, and the values are read when the switches open. (The "init" switch position in TABLE 6 refers to corresponding "init density" and "init viscosity" switch positions in FIG. 12 which respectively represent the initial or user input density and viscosity.)

TABLE 6

Mode Matrix of the Calculate Fluid Parameters Dispense Submode of FIG. 12

| MODE | SW1 | SW2 | SW3 | SW4 | SW5 | SW6 | SW7 | SW8 | SW9 | SW10 |
|---|---|---|---|---|---|---|---|---|---|---|
| Measure Po | open | closed | closed | init | init | open | open | open | open | X |
| Measure P1 | open | open | closed | init | init | open | open | open | open | X |
| Measure Pss | open | open | open | init | init | open | open | open | open | X |

The transient pressure measurement scheme, as described above, is used to estimate or determine the density and/or viscosity. The pressure Po as measured by the pressure sensor(s) 50 is communicated to the 162. The nozzle 38 is positioned over the waste position 31 and the stepper motor 26 (and syringe pump 22) are incremented or operated in the forward direction to dispense fluid. The control block or system element 140 communicates stepper frequency (and stepper step size) commands to the stepper motor 26. The valve 20 is also provided with commands from the control block or system element 140 to operate the valve 20 at a predetermined valve on or open time, valve open frequency and/or duty cycle.

After a time t1, the pressure P1 as measured by the pressure sensor(s) is communicated to the control block or system element 162. This pressure P1 can be an average value to reduce signal noise. Dispensing is continued for a long time until the pressure reaches or decays to a steady state value Pss at time tss. This steady state pressure is communicated to the control block element 162. The valve open time Tv, the valve open frequency Fvalve and the stepper flow rate Qstep are provided to the control block or system element 162. The control block or system element 162 computes the capillary flow resistance Rc and orifice flow resistance Ro using equations (47) to (49) and communicates these values to the control block or system element 164. The control block or system element 164 is also provided with the nominal nozzle diameter D_nom, the nominal nozzle length L_nom and the nozzle discharge coefficient Cd. The control block or system element 164 computes the estimated fluid density and viscosity using equations (51) and (52).

Once the values of the fluid density and viscosity are estimated, these values are communicated to the control block or system element 140. This is illustrated below by the Hold submode TABLE 7. Note that all inputs in TABLE 7 are sample and hold, and the values are read when the switches open. (The "calc" switch position in TABLE 7 refers to corresponding "init density" and "init viscosity" switch positions in FIG. 12 which respectively represent the initial or user input density and viscosity.)

TABLE 7

Hold Mode to Transfer Calculated Fluid Parameters

| MODE | SW1 | SW2 | SW3 | SW4 | SW5 | SW6 | SW7 | SW8 | SW9 | SW10 |
|---|---|---|---|---|---|---|---|---|---|---|
| Hold | open | open | open | calc | calc | open | open | open | open | X |

Figure 14:
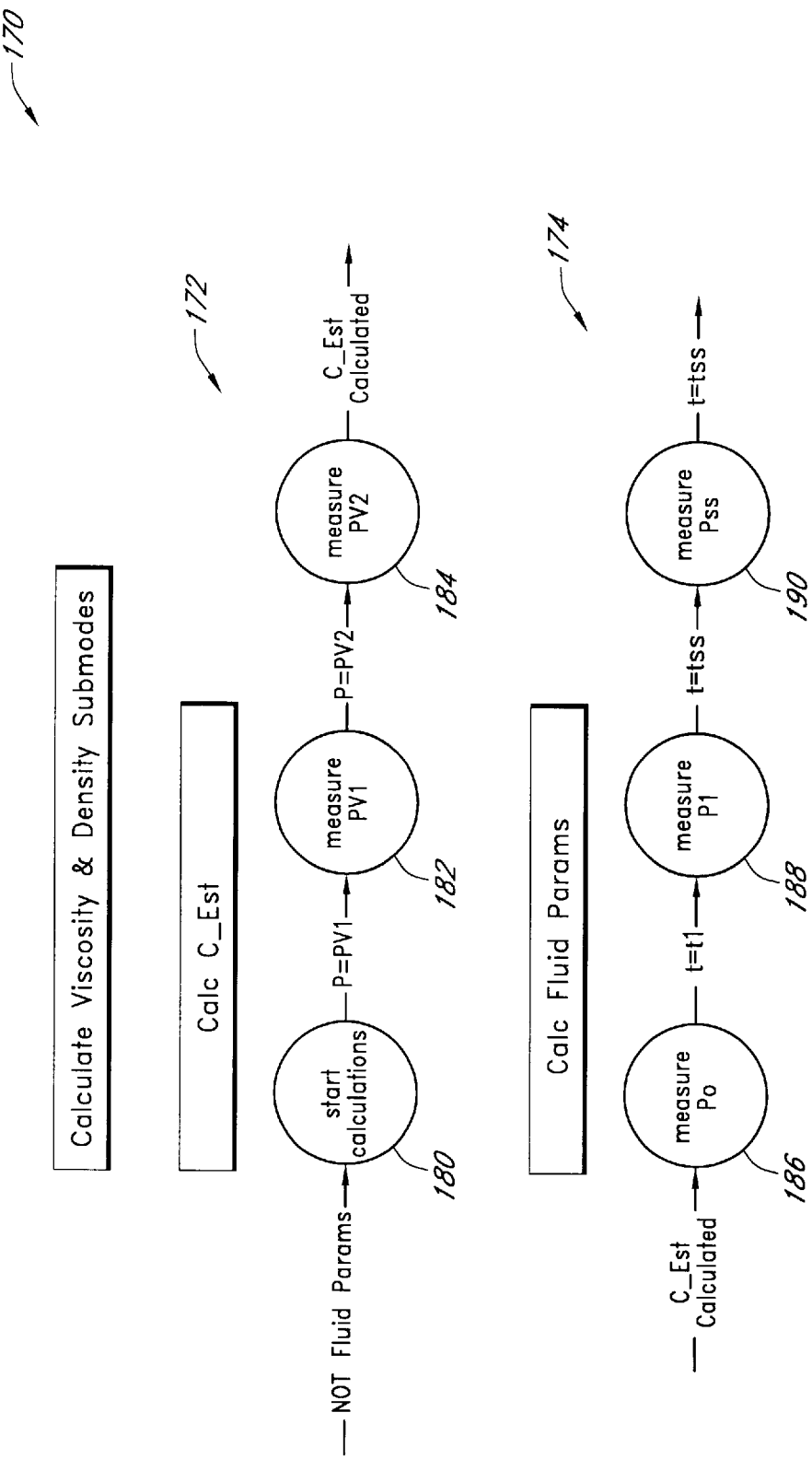
FIG. 14 is a detailed schematic of the state diagram of FIG. 13 having features in accordance with one preferred embodiment of the present invention.

The operations of FIG. 12 to determine the elastic capacitance and the fluid density and viscosity can also be represented by the state diagrams of FIGS. 13 and 14. FIG. 13 is a simplified state diagram 170 schematically, illustrating the operation of the fluid parameter calculator 142. If the fluid density, viscosity and system compliance are not available, the system compliance is determined in step 172. Then in step 174, the fluid density and fluid viscosity are calculated. In step 176, the calculated or estimated values of the density and viscosity are communicated to the control block or system elements 140 and/or 146.

FIG. 14 is a more detailed schematic of the state diagram 170 of FIG. 13. Step 172 comprises a step 180 of starting the calculations, a step 182 of measuring the initial pressure PV1 and a step 184 of measuring the second predetermined pressure PV2 achieved by the actuations of the syringe pump 22. This allows the elastic capacitance to be calculated as discussed above.

The system pressure is then reset to the initial pressure Po. Step 174 comprises a step 186 of measuring the initial pressure Po, a step 188 of measuring the pressure PI at a later time t1 and a step 190 of measuring the steady state pressure Pss at a time tss. The fluid density and viscosity are then calculated based on these transient pressure measurements and other parameters.

Surface Tension

If the surface tension is not known, it can be estimated using an off-line calibration or operation. Drops of gradually decreasing size are dispensed and the detachment from the nozzle 38 is observed by the user. At the onset or close to the onset of unreliable and/or improper drop detachment, it can be assumed that the Weber number is close to 1; that is, We≅1. Equation (58) and/or other suitable equation, model or correlation can then be used to estimate the fluid surface tension σ.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A method of actively controlling a fluid delivery system comprising a dispenser hydraulically arranged in series with a direct current fluid source, said method comprising the steps of:
   determining a steady state dispense pressure based on the fluid dynamical characteristic equations of said system;
   causing said steady state dispense pressure to exist within said system by operating said direct current fluid source; and
   actuating said dispenser and said direct current fluid source to dispense precise and/or predetermined quantities of a fluid onto a target, each of said quantities of fluid being dispensed in the form of one or more droplets.

2. The method of claim 1, further comprising the step of monitoring the pressure within said system by using a pressure sensor.

3. The method of claim 2, wherein said pressure sensor is placed on said dispenser.

4. The method of claim 2, wherein said pressure sensor is placed intermediate said dispenser and said direct current fluid source.

5. The method of claim 1, further comprising the step of calculating the density of said fluid.

6. The method of claim 1, further comprising the step of calculating the viscosity of said fluid.

7. The method of claim 1, further comprising the step of aspirating a predetermined quantity of fluid from a source.

8. The method of claim 7, further comprising the step of determining a steady state aspirate pressure based on the fluid dynamical characteristic equations of said system.

9. The method of claim 8, further comprising the step of causing said steady state aspirate pressure to exist within said system by operating said direct current fluid source.

10. The method of claim 9, further comprising the step of monitoring the pressure within said system.

11. The method of claim 1, further comprising the step of providing relative motion between said dispenser and said target.

12. The method of claim 1, wherein said dispenser comprises a solenoid-actuated dispenser.

13. The method of claim 1, wherein said dispenser comprises a drop-on-demand valve.

14. The method of claim 1, wherein said direct current fluid source comprises a positive displacement device.

15. The method of claim 1, wherein said direct current fluid source comprises a syringe pump.

16. The method of claim 1, wherein said step of determining a steady state dispense pressure comprises the step of estimating the fluid density.

17. The method of claim 1, wherein said step of determining a steady state dispense pressure comprises the step of estimating the fluid viscosity.

18. The method of claim 1, further comprising the step of selecting a volume of said droplets of said fluid to be dispensed onto said target.

19. The method of claim 18, further comprising the step of adjusting said dispense pressure to dispense droplets of varying size and/or exit velocity.

20. The method of claim 19, further comprising the step of providing relative motion between said dispenser and said target to dispense predetermined quantities of said fluid onto predetermined locations on said target.

21. The method of claim 1, wherein said target comprises a glass slide.

22. The method of claim 1, wherein said target comprises a substrate.

23. The method of claim 1, wherein said target comprises a membrane.

24. The method of claim 1, wherein said target comprises a single-well receptacle.

25. The method of claim 1, wherein said target comprises a multi-well microtiter plate.

26. The method of claim 1, wherein said target comprises at least one of a glass slide, a substrate, a membrane, a single-well receptacle and a multi-well microtiter plate.

27. The method of claim 1, further comprising the step of monitoring the system pressure and adjusting the system pressure and/or operational parameters in response to any substantial deviations of the system pressure from the steady state dispense pressure.

28. The method of claim 1, further comprising the step of estimating and monitoring the Reynolds number.

29. The method of claim 1, further comprising the step of estimating and monitoring the Weber number.

30. The method of claim 1, further comprising the step of estimating and monitoring the fluid exit velocity.

31. The method of claim 1, further comprising the step of estimating and monitoring the system compliance.

32. The method of claim 1, wherein said quantities of said fluid are ejected in the form of one or more droplets from a nozzle of a dispensing tip of said dispenser.

33. The method of claim 32, wherein the step of determining a steady state dispense pressure comprises the steps of:

estimating the capillary flow resistance (Rc) and orifice flow resistance (Ro) of the nozzle; and calculating the fluid pressure drop through the nozzle during generally steady state dispensing to estimate the steady state dispense pressure (Pss) using the relationship:

$$Pss = QRc + (QRo)^2$$

where, Q is the flow rate.

34. The method of claim 33, wherein the step of estimating the capillary flow resistance (Rc) and orifice flow resistance (Ro) of the nozzle comprises computing Rc and Ro based on the relationships:

$$Rc = \frac{8\mu L}{\pi \left(\frac{D}{2}\right)}$$

where, $\mu$ is the fluid viscosity, L is the nominal nozzle length and D is the nominal nozzle diameter; and $$Ro = \frac{\sqrt{\frac{\rho}{2}}}{Cd\pi\left(\frac{D}{2}\right)^2}$$

where, $\rho$ is the fluid density and Cd is the nozzle discharge coefficient.

35. The method of claim 1, wherein the step of determining a steady state dispense pressure comprises the steps of:

estimating the resistance to fluid flow through the system by perturbing or modulating the flow rate about the desired flow rate to estimate the capillary flow resistance (Rc) and orifice flow resistance (Ro); and calculating the fluid pressure drop during dispensing to estimate the steady state dispense pressure (Pss) using the relationship:

$$Pss = QRc + (QRo)^2$$

where, Q is the flow rate.

36. The method of claim 35, wherein the step of estimating the resistance to fluid flow through the system comprises the steps of:

making two measurements of the system pressure at two flow rates during substantially steady state dispensing; and computing Rc and Ro based on the relationships:

$$Rc = \frac{PlQh^2 - PhQl^2}{QhQl(Qh - Ql)}$$

$$Ro = \sqrt{\frac{PhQl - PlQh}{QhQl(Qh - Ql)}}$$

where, Ql is a lower perturbed flow rate, Qh is a higher perturbed flow rate, Pl is the pressure measurement at Ql and Ph is the pressure measurement at Qh.

37. The method of claim 36, further comprising the step of estimating the fluid viscosity ($\mu$) based on the relationship:

$$\mu = \frac{\pi Rc \left(\frac{D}{2}\right)^4}{8L}$$

where, D is the nominal diameter of a nozzle of a dispensing tip of said dispenser and L is a nominal length of the nozzle.

38. The method of claim 36, further comprising the step of estimating the fluid density ($\rho$) based on the relationship:

$$\rho = 2\left(\pi Cd \frac{D^2}{4} Ro\right)^2$$

where, D is the nominal diameter of a nozzle of a dispensing tip of said dispenser and Cd is the nozzle discharge coefficient.

39. The method of claim 1, further comprising the step of estimating the fluid viscosity ($\mu$) and fluid density ($\rho$) using transient pressure measurements.

40. The method of claim 39, wherein the step of estimating the fluid viscosity ($\mu$) and fluid density ($\rho$) comprises the step of estimating the resistance to fluid flow by computing the capillary flow resistance (Rc) and orifice flow resistance (Ro) based on the linearized pressure equations for an initial pressure of Po at the time that pulsed dispensing operation begins and decays to a steady state value of Pss, whereby:

$$Rc = \frac{Fvalve}{Qstep}\left(2PssTv - \frac{Qstep\tau}{FvalveC}\right)$$

$$Ro = \frac{Fvalve}{Qstep}\sqrt{\left(\frac{Qstep\tau}{CFvalve} - PssTv\right)Tv}$$

where, Fvalve is the open-close frequency of the dispenser, Tv is the dispenser open time, Qstep is the flow rate provided by the direct current fluid source, C is the elastic capacitance or compliance, $\tau$ is the system time constant and is given by:

$$\tau = \frac{t1}{\ln(|Po - Pss|) - \ln(|Pl - Pss|)} FvalveTv$$

where, Pl is the measured pressure during decay at an intermediate time t1.

41. The method of claim 40, further comprising the step of estimating the fluid viscosity ($\mu$) based on the relationship:

$$\mu = \frac{\pi Rc\left(\frac{D}{2}\right)^4}{8L}$$

where, D is the nominal diameter of a nozzle of a dispensing tip of said dispenser and L is a nominal length of the nozzle.

42. The method of claim 40, further comprising the step of estimating the fluid density ($\rho$) based on the relationship:

$$\rho = 2\left(\pi Cd\frac{D^2}{4}Ro\right)^2$$

where, D is the nominal diameter of a nozzle of a dispensing tip of said dispenser and Cd is the nozzle discharge coefficient.

43. The method of claim 1, wherein said fluid comprises a liquid reagent.

44. A method of actively controlling a fluid delivery system comprising a dispenser hydraulically arranged in series with a direct current fluid source, said method comprising the steps of:
   determining a steady state dispense pressure based on the fluid dynamical characteristic equations of said system;
   causing said steady state dispense pressure to exist within said system by operating said direct current fluid source;
   actuating said dispenser and said direct current fluid source to dispense precise and/or predetermined quantities of a fluid onto a target; and
   aspirating a predetermined quantity of fluid from a source.

45. The method of claim 44, further comprising determining a steady state aspirate pressure based on the fluid dynamical characteristic equations of said system.

46. The method of claim 45, further comprising causing said steady state aspirate pressure to exist within said system by operating said direct current fluid source.

47. The method of claim 46, further comprising monitoring the pressure within said system.

48. The method of claim 44, further comprising providing relative motion between said dispenser and said target and/or said source.

49. The method of claim 44, wherein said fluid comprises a liquid reagent.

50. A method of actively controlling a fluid delivery system comprising a dispenser hydraulically arranged in series with a direct current fluid source, said method comprising the steps of:
   determining a steady state dispense pressure based on the fluid dynamical characteristic equations of said system;
   causing said steady state dispense pressure to exist within said system by operating said direct current fluid source;
   actuating said dispenser and said direct current fluid source to dispense precise and/or predetermined quantities of a fluid onto a target; and
   estimating and monitoring the Reynolds number.

51. The method of claim 50, wherein the step of estimating and monitoring the Reynolds number comprises estimating the fluid viscosity.

52. The method of claim 51, wherein the step of estimating and monitoring the Reynolds number comprises estimating the fluid density.

53. The method of claim 52, wherein the step of estimating and monitoring the Reynolds number comprises estimating the fluid flow velocity.

54. The method of claim 50, wherein said dispenser comprises a solenoid-actuated dispenser.

55. The method of claim 50, wherein said fluid comprises a liquid reagent.

56. A method of actively controlling a fluid delivery system comprising a dispenser hydraulically arranged in series with a direct current fluid source, said method comprising the steps of:
   determining a steady state dispense pressure based on the fluid dynamical characteristic equations of said system;
   causing said steady state dispense pressure to exist within said system by operating said direct current fluid source;
   actuating said dispenser and said direct current fluid source to dispense precise and/or predetermined quantities of a fluid onto a target; and
   estimating and monitoring the Weber number.

57. The method of claim 56, wherein the step of estimating and monitoring the Weber number comprises estimating the fluid surface tension.

58. The method of claim 57, wherein the step of estimating and monitoring the Weber number comprises estimating the fluid density.

59. The method of claim 58, wherein the step of estimating and monitoring the Weber number comprises estimating the fluid flow velocity.

60. The method of claim 56, further comprising providing relative motion between said dispenser and said target.

61. The method of claim 56, wherein said direct current fluid source comprises a positive displacement pump.

62. A method of actively controlling a fluid delivery system comprising a dispenser hydraulically arranged in series with a direct current fluid source, said method comprising the steps of:
   determining a steady state dispense pressure based on the fluid dynamical characteristic equations of said system;
   causing said steady state dispense pressure to exist within said system by operating said direct current fluid source;
   actuating said dispenser and said direct current fluid source to dispense precise and/or predetermined quantities of a fluid onto a target; and
   estimating and monitoring the system compliance.

63. The method of claim 62, wherein the system compliance (C) is estimated using the relationship:

$$C = \frac{\Delta V}{\Delta P}$$

where, V is the volume and P is the pressure.

64. The method of claim 63, wherein the system compliance (C) is iteratively estimated.

65. The method of claim 62, wherein the system compliance (C) is estimated using the relationship:

$$\frac{dP}{dt} = \frac{Q}{C}$$

where, P is the pressure, t is time and Q is the flow rate.

66. The method of claim 62, further comprising adjusting said dispense pressure to dispense droplets of varying size and/or exit velocity.

67. The method of claim 66, further comprising providing relative motion between said dispenser and said target to dispense predetermined quantities of said fluid onto predetermined locations on said target.

68. A method of actively controlling a fluid delivery system comprising a dispenser hydraulically arranged in series with a direct current fluid source, said method comprising the steps of:

determining a steady state dispense pressure based on the fluid dynamical characteristic equations of said system, comprising the steps of:

estimating the resistance to fluid flow through the system by perturbing or modulating the flow rate about the desired flow rate to estimate the capillary flow resistance (Rc) and orifice flow resistance (Ro); and calculating the fluid pressure drop during dispensing to estimate the steady state dispense pressure (Pss) using the relationship:

$$Pss = QRc + (QRo)^2$$

where, Q is the flow rate;

causing said steady state dispense pressure to exist within said system by operating said direct current fluid source; and actuating said dispenser and said direct current fluid source to dispense precise and/or predetermined quantities of a fluid onto a target.

69. The method of claim 68, wherein the step of estimating the resistance to fluid flow through the system comprises the steps of:

making two measurements of the system pressure at two flow rates during substantially steady state dispensing; and computing Rc and Ro based on the relationships:

$$Rc = \frac{PlQh^2 - PhQl^2}{QhQl(Qh - Ql)}$$

$$Ro = \sqrt{\frac{PhQl - PlQh}{QhQl(Qh - Ql)}}$$

where, Ql is a lower perturbed flow rate, Qh is a higher perturbed flow rate, Pl is the pressure measurement at Ql and Ph is the pressure measurement at Qh.

70. The method of claim 69, further comprising estimating the fluid viscosity ($\mu$) based on the relationship:

$$\mu = \frac{\pi Rc \left(\frac{D}{2}\right)^4}{8L}$$

where, D is the nominal diameter of a nozzle of a dispensing tip of said dispenser and L is a nominal length of the nozzle.

71. The method of claim 69, further comprising estimating the fluid density ($\rho$) based on the relationship:

$$\rho = 2\left(\pi Cd \frac{D^2}{4} Ro\right)^2$$

where, D is the nominal diameter of a nozzle of a dispensing tip of said dispenser and Cd is the nozzle discharge coefficient.

72. The method of claim 68, wherein said dispenser comprises a drop-on-demand valve.

73. The method of claim 72, wherein said dispenser comprises a micro-solenoid valve.

74. A method of actively controlling a fluid delivery system comprising a dispenser hydraulically arranged in series with a direct current fluid source, said method comprising the steps of:

determining a steady state dispense pressure based on the fluid dynamical characteristic equations of said system;

causing said steady state dispense pressure to exist within said system by operating said direct current fluid source; and actuating said dispenser and said direct current fluid source to dispense precise and/or predetermined quantities of a fluid onto a target; and estimating the fluid viscosity ($\mu$) and fluid density ($\rho$) using transient pressure measurements.

75. The method of claim 74, wherein estimating the fluid viscosity ($\mu$) and fluid density ($\rho$) comprises the step of estimating the resistance to fluid flow by computing the capillary flow resistance (Rc) and orifice flow resistance (Ro) based on the linearized pressure equations for an initial pressure of Po at the time that pulsed dispensing operation begins and decays to a steady state value of Pss, whereby:

$$Rc = \frac{Fvalve}{Qstep}\left(2PssTv - \frac{Qstep\tau}{FvalveC}\right)$$

$$Ro = \frac{Fvalve}{Qstep}\sqrt{\left(\frac{Qstep\tau}{CFvalve} - PssTv\right)Tv}$$

where, Fvalve is the open-close frequency of the dispenser, Tv is the dispenser open time, Qstep is the flow rate provided by the direct current fluid source, C is the elastic capacitance or compliance, $\tau$ is the system time constant and is given by:

$$\tau = \frac{t1}{\ln(|Po - Pss|) - \ln(|P1 - Pss|)} FvalveTv$$

where, P1 is the measured pressure during decay at an intermediate time t1.

76. The method of claim 75, further comprising estimating the fluid viscosity ($\mu$) based on the relationship:

$$\mu = \frac{\pi Rc \left(\frac{D}{2}\right)^4}{8L}$$

where, D is the nominal diameter of a nozzle of a dispensing tip of said dispenser and L is a nominal length of the nozzle.

77. The method of claim 75, further comprising estimating the fluid density ($\rho$) based on the relationship:

$$\rho = 2\left(\pi Cd \frac{D^2}{4} Ro\right)^2$$

where, D is the nominal diameter of a nozzle of a dispensing tip of said dispenser and Cd is the nozzle discharge coefficient.

78. The method of claim 74, further comprising monitoring the system pressure.

79. The method of claim 78, further comprising adjusting the system pressure and/or operational parameters in response to any substantial deviations of the system pressure from the steady state dispense pressure.

80. The method of claim 79, wherein said fluid comprises a liquid reagent.

* * * * *